(12) United States Patent
Delattre et al.

(10) Patent No.: US 10,267,726 B2
(45) Date of Patent: Apr. 23, 2019

(54) SYSTEMS AND METHODS OF IDENTIFYING AND/OR TRACKING PARTICLES IN A DROPLET, WHEREIN THE PARTICLE CAN BE A CELL

(71) Applicants: ILLUMINA FRANCE SARL, Paris (FR); COMMISSARIAT À L'ÉNERGIE ATOMIQUE ET AUX ÉNERGIES ALTERNATIVES, Paris (FR)

(72) Inventors: Cyril Delattre, San Diego, CA (US); Arnaud Rival, Paris (FR); Cédric Allier, Paris (FR)

(73) Assignees: ILLUMINA FRANCE SARL, Paris (FR); COMMISSARIAT À L'ÉNERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/564,416

(22) PCT Filed: Apr. 26, 2016

(86) PCT No.: PCT/IB2016/000687
§ 371 (c)(1),
(2) Date: Oct. 4, 2017

(87) PCT Pub. No.: WO2016/174523
PCT Pub. Date: Nov. 3, 2016

(65) Prior Publication Data
US 2018/0136114 A1     May 17, 2018

Related U.S. Application Data

(60) Provisional application No. 62/171,603, filed on Jun. 5, 2015, provisional application No. 62/153,118, filed on Apr. 27, 2015.

(51) Int. Cl.
| G01N 21/17 | (2006.01) |
| G01N 15/14 | (2006.01) |
| G01N 15/10 | (2006.01) |
| G01N 15/00 | (2006.01) |

(52) U.S. Cl.
CPC ......... *G01N 21/17* (2013.01); *G01N 15/1429* (2013.01); *G01N 15/1434* (2013.01); (Continued)

(58) Field of Classification Search
CPC .............. G01N 21/1434; G01N 21/17; G01N 15/1475; G01N 15/1429; G01N 15/1463; (Continued)

(56) References Cited

U.S. PATENT DOCUMENTS

2007/0242105 A1* 10/2007 Srinivasan .......... B01F 13/0071
                                                                    347/63
2011/0186433 A1* 8/2011 Pollack .................. G01N 35/10
                                                                    204/549
(Continued)

FOREIGN PATENT DOCUMENTS

WO       2015031849 A1    3/2015

OTHER PUBLICATIONS

Li et al., "Bubble-based droplet mixers microfluidic systems", IEEE 24th International Conference on Micro Electro Mechanical Systems (MEMS 2011), IEEE, US, Jan. 23, 2011, pp. 1127-1130éà.
(Continued)

*Primary Examiner* — Sang H Nguyen
(74) *Attorney, Agent, or Firm* — Illumina, Inc.

(57) ABSTRACT

In accordance with embodiments herein, microfluidics systems and methods are described for identifying and/or tracking particles in a droplet. For example, the particle may be a bead, a cell, or any other type of particle. For example, embodiments herein are useful in distinguishing cells from other particles. The microfluidics systems and methods
(Continued)

provide the capability to image a large area (e.g., a few square millimeters) within a digital fluidics chamber using interference microscopy, wherein the image of the interference pattern is acquired, instead of an image of the micrometric object itself. The interference pattern results from the incoming light that interferes with the light scattered by the object. In the case of micrometric objects (e.g., cells, bacteria, etc.), the acquired interference pattern may typically be about 100 jum in diameter so that the area can be imaged using a lens-free imaging configuration or using a low magnification lens.

20 Claims, 21 Drawing Sheets

(52) U.S. Cl.
CPC ..... *G01N 15/1475* (2013.01); *G01N 15/1463* (2013.01); *G01N 2015/0053* (2013.01); *G01N 2015/1006* (2013.01); *G01N 2015/1481* (2013.01); *G01N 2021/1765* (2013.01)

(58) Field of Classification Search
CPC ....... G01N 2015/1006; G01N 15/0053; G01N 2015/1481; G01N 2021/1765
See application file for complete search history.

(56) References Cited

U.S. PATENT DOCUMENTS

| | | | | |
|---|---|---|---|---|
| 2012/0136147 | A1* | 5/2012 | Winger | C12Q 1/25 536/123.1 |
| 2012/0325665 | A1* | 12/2012 | Chiou | B03C 5/005 204/601 |
| 2013/0116128 | A1* | 5/2013 | Shen | B01L 3/502792 506/2 |
| 2015/0153558 | A1* | 6/2015 | Ozcan | G01B 9/04 348/79 |
| 2016/0299101 | A1* | 10/2016 | Pantoja | C12Q 1/6869 |
| 2016/0334616 | A1* | 11/2016 | Vayser | G02B 6/241 |

OTHER PUBLICATIONS

Eidmann, Authorized Officer, European Patent Office, International Search Report and Written Opinion, International Application No. PCT/IB2016/000687, dated Sep. 15, 2016.

Huang, et al., "Optoelectronic tweezers integrated with lensefree holographic microscopy for wild-filed interactive cell and particle manipulation on a chip," Lab on a Chip: Miniaturisation for Chemistry, Physics, Biology, Materials Science and Bioengineering, vol. 13(12), Jan. 1, 2013, 2278-2284.

\* cited by examiner

US 10,267,726 B2

SYSTEMS AND METHODS OF IDENTIFYING AND/OR TRACKING PARTICLES IN A DROPLET, WHEREIN THE PARTICLE CAN BE A CELL

CROSS-REFERENCE TO RELATED APPLICATIONS

The present application is a 35 U.S.C. § 371 National Stage application of International Patent Application No. PCT/IB2016/000687, filed on Apr. 26, 2016, which further claims the benefit of U.S. Provisional Patent Application No. 62/171,603, filed on Jun. 5, 2015, and U.S. Provisional Patent Application No. 62/153,118, filed on Apr. 27, 2015, each of which are incorporated herein by reference in their entirety.

BACKGROUND OF THE INVENTION

A droplet actuator is an example of digital fluidics technology. A droplet actuator typically includes one or more substrates configured to form a surface or gap for conducting droplet operations. The one or more substrates establish a droplet operations surface or gap for conducting droplet operations and may also include electrodes arranged to conduct the droplet operations via electrowetting. The droplet operations substrate or the gap between the substrates may be coated or filled with a filler fluid that is immiscible with the liquid that forms the droplets.

Optical detection systems are used with digital fluidics technology, such as with droplet actuators. The standard microscopy used in these optical detection systems remains a compromise between resolution, field of depth, and field of view. For example, using a low magnification objective (e.g., a 5× objective), the field of view is about 1 millimeter square, the field of depth is a few microns, and the resolution is a few microns. Hence, in order to capture at glance a microfluidic chamber, of which the footprint may often range from a few square millimeters to a few square centimeters and the thickness from a few microns to millimeters, standard microscopy must be motorized in order to scan both the X-Y plane and the Z focal plane. Consequently, a drawback of using standard microscopy for optical detection in, for example, a droplet actuator is the long acquisition time (a few seconds to a minute), which prevents fast time-lapse acquisition.

Definitions

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating current (AC) or direct current (DC). Any suitable voltage may be used. For example, an electrode may be activated using a voltage which is greater than about 150 V, or greater than about 200 V, or greater than about 250 V, or from about 275 V to about 1000 V, or about 300 V. Where an AC signal is used, any suitable frequency may be employed. For example, an electrode may be activated using an AC signal having a frequency from about 1 Hz to about 10 MHz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Particles detected according to the invention may in some cases be beads. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a flow path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in Watkins et al., U.S. Patent Pub. No. 20050260686, entitled "Multiplex Flow Assays Preferably with Magnetic Particles as Solid Phase," published on Nov. 24, 2005; Chandler., U.S. Patent Pub. No. 20030132538, entitled "Encapsulation of Discrete Quanta of Fluorescent Particles," published on Jul. 17, 2003; Chandler et al., U.S. Patent Pub. No. 20050118574, entitled "Multiplexed Analysis of Clinical Specimens Apparatus and Method," published on Jun. 2, 2005; Chandler et al., U.S. Patent Pub. No. 20050277197, entitled "Microparticles with Multiple Fluorescent Signals and Methods of Using Same," published on Dec. 15, 2005; and Chandler et al., U.S. Patent Pub. No. 20060159962, entitled "Magnetic Microspheres for use in Fluorescence-based Applications," published on Jul. 20, 2006, the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in Pollack et al., U.S. Patent Pub. No. 20080053205, entitled "Droplet-Based Particle Sorting," published on Mar. 6, 2008; U.S. Patent App. No. 61/039,183, entitled "Multiplexing Bead Detection in a Single Droplet," filed on Mar. 25, 2008; Pamula et al., U.S. Patent App. No. 61/047,789, entitled "Droplet Actuator Devices and Droplet Operations Using Beads," filed on Apr. 25, 2008; U.S. Patent App. No. 61/086,183, entitled "Droplet Actuator Devices and Methods for Manipulating Beads," filed on Aug. 5, 2008; Eckhardt et al., International Patent Pub. No. WO/2008/098236, entitled "Droplet Actuator Devices and Methods Employing Magnetic Beads," published on Aug. 14, 2008; Grichko et al., International Patent Pub. No. WO/2008/134153, entitled "Bead-based Multiplexed Analytical Methods and Instrumentation," published on Nov. 6, 2008; Eckhardt et al., International Patent Pub. No. WO/2008/116221, "Bead Sorting on a Droplet Actuator," published on Sep. 25, 2008; and Eckhardt et al., International Patent Pub. No. WO/2007/120241, entitled "Droplet-based Biochemistry," published on Oct. 25, 2007, the entire disclosures of which are incorporated herein by reference. Bead characteristics may be employed in the multiplexing aspects of the present disclosure. Examples of beads having characteristics suitable for multiplexing, as well as methods of detecting and analyzing signals emitted from such beads, may be found in Whitman et al., U.S. Patent Pub. No. 20080305481, entitled "Systems and Methods for Multiplex Analysis of PCR in Real Time," published on Dec. 11, 2008; Roth, U.S. Patent Pub. No. 20080151240, "Methods and Systems for Dynamic Range Expansion," published on Jun. 26, 2008; Sorensen et al., U.S. Patent Pub. No. 20070207513, entitled "Methods, Products, and Kits for Identifying an Analyte in a Sample," published on Sep. 6, 2007; Roth, U.S. Patent Pub. No. 20070064990, entitled "Methods and Systems for Image Data Processing," published on Mar. 22, 2007; Chandler et al., U.S. Patent Pub. No. 20060159962, entitled "Magnetic Microspheres for use in Fluorescence-based Applications," published on Jul. 20, 2006; Chandler et al., U.S. Patent Pub. No. 20050277197, entitled "Microparticles with Multiple Fluorescent Signals and Methods of Using Same," published on Dec. 15, 2005; and Chandler et al., U.S. Patent Publication No. 20050118574, entitled "Multiplexed Analysis of Clinical Specimens Apparatus and Method," published on Jun. 2, 2005, the entire disclosures of which are incorporated herein by reference.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the present disclosure, see Eckhardt et al., International Patent Pub. No. WO/2007/120241, entitled, "Droplet-Based Biochemistry," published on Oct. 25, 2007, the entire disclosure of which is incorporated herein by reference. Pursuant to various embodiments of the invention, particles may be detected in droplets.

In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Cells present in the foregoing biological samples may be detected in accordance with various aspects of the invention. Moreover, a droplet may include a reagent, such as water, deionized water, saline solutions, acidic solutions, basic solutions, detergent solutions and/or buffers. A droplet can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., *Nature* 456:53-59 (2008); Gormley et al., International Patent Pub. No. WO/2013/131962, entitled, "Improved Methods of Nucleic Acid Sequencing," published on Sep. 12, 2013; Barnes et al., U.S. Pat. No. 7,057,026, entitled "Labelled Nucleotides," issued on Jun. 6, 2006; Kozlov et al., International Patent Pub. No. WO/2008/042067, entitled, "Compositions and Methods for Nucleotide Sequencing," published on Apr. 10, 2008; Rigatti et al., International Patent Pub. No. WO/2013/117595, entitled, "Targeted Enrichment and Amplification of Nucleic Acids on a Support," published on Aug. 15, 2013; Hardin et al., U.S. Pat. No. 7,329,492, entitled "Methods for Real-Time Single Molecule Sequence Fetermination," issued on Feb. 12, 2008; Hardin et al., U.S. Pat. No. 7,211,414, entitled "Enzymatic Nucleic Acid Synthesis: Compositions and Methods for Altering Monomer Incorporation Fidelity," issued on May 1, 2007; Turner et al., U.S. Pat. No. 7,315,019, entitled "Arrays of Optical Confinements and Uses Thereof," issued on Jan. 1, 2008; Xu et al., U.S. Pat. No. 7,405,281, entitled "Fluorescent Nucleotide Analogs and Uses Therefor," issued on Jul. 29, 2008; and Rank et. al., U.S. Patent Pub. No. 20080108082, entitled "Polymerase Enzymes and Reagents for Enhanced Nucleic Acid Sequencing," published on May 8, 2008, the entire disclosures of which are incorporated herein by reference; enzymes such as polymerases, ligases, recombinases, or transposases; binding partners such as antibodies, epitopes, streptavidin, avidin, biotin, lectins or carbohydrates; or other biochemically active molecules. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids. A droplet may include one or more beads.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. Patent Pub. No. 20060194331, entitled "Apparatuses and Methods for Manipulating Droplets on a Printed Circuit Board," published on Aug. 31, 2006; Pollack et al., International Patent Pub. No. WO/2007/120241, entitled "Droplet-Based Biochemistry," published on Oct. 25, 2007; Shenderov, U.S.

Pat. No. 6,773,566, entitled "Electrostatic Actuators for Microfluidics and Methods for Using Same," issued on Aug. 10, 2004; Shenderov, U.S. Pat. No. 6,565,727, entitled "Actuators for Microfluidics Without Moving Parts," issued on May 20, 2003; Kim et al., U.S. Patent Pub. No. 20030205632, entitled "Electrowetting-driven Micropumping," published on Nov. 6, 2003; Kim et al., U.S. Patent Pub. No. 20060164490, entitled "Method and Apparatus for Promoting the Complete Transfer of Liquid Drops from a Nozzle," published on Jul. 27, 2006; Kim et al., U.S. Patent Pub. No. 20070023292, entitled "Small Object Moving on Printed Circuit Board," published on Feb. 1, 2007; Shah et al., U.S. Patent Pub. No. 20090283407, entitled "Method for Using Magnetic Particles in Droplet Microfluidics," published on Nov. 19, 2009; Kim et al., U.S. Patent Pub. No. 20100096266, entitled "Method and Apparatus for Real-time Feedback Control of Electrical Manipulation of Droplets on Chip," published on Apr. 22, 2010; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker et al., U.S. Pat. No. 7,641,779, entitled "Method and Apparatus for Programmable Fluidic Processing," issued on Jan. 5, 2010; Becker et al., U.S. Pat. No. 6,977,033, entitled "Method and Apparatus for Programmable Fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, U.S. Patent Pub. No. 20110048951, entitled "Digital Microfluidics Based Apparatus for Heat-exchanging Chemical Processes," published on Mar. 3, 2011; Fouillet et al., U.S. Patent Pub. No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between Two or Several Solid Substrates," published on Aug. 18, 2005; and Dhindsa et al., "Virtual Electrowetting Channels: Electronic Liquid Transport with Continuous Channel Functionality," Lab Chip, 10:832-836 (2010), the entire disclosures of which are incorporated herein by reference. Certain droplet actuators will include one or more substrates arranged with a droplet operations gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the present disclosure.

During droplet operations it is preferred that droplets remain in continuous contact or frequent contact with a ground or reference electrode. A ground or reference electrode may be associated with the top substrate facing the gap, the bottom substrate facing the gap, and/or in the gap. When electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap there between and define on-actuator dispensing reservoirs. The spacer height may, for example, be at least about 5 µm, 100 µm, 200 µm, 250 µm, 275 µm or more. Alternatively or additionally the spacer height may be at most about 600 µm, 400 µm, 350 µm, 300 µm, or less. The spacer may, for example, be formed of a layer of projections from the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowing through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap.

Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the present disclosure include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential.

In certain embodiments, combinations of two or more of the foregoing techniques may be employed to conduct a droplet operation in a droplet actuator of the present disclosure. Similarly, one or more of the foregoing may be used to deliver liquid into a droplet operations gap, e.g., from a reservoir in another device or from an external reservoir of the droplet actuator (e.g., a reservoir associated with a droplet actuator substrate and a flow path from the reservoir into the droplet operations gap). Droplet operations surfaces of certain droplet actuators of the present disclosure may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), other fluorinated monomers for plasma-enhanced chemical vapor deposition (PECVD), and organosiloxane (e.g., SiOC) for PECVD.

In some cases, the droplet operations surface may include a hydrophobic coating having a thickness ranging from about 10 nm to about 1,000 nm. In some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene) poly(styrenesulfonate) (PEDOT:PSS). Other examples of electrically conducting organic polymers and alternative conductive layers are described in Pollack et al., International Patent Pub. No. WO/2011/002957, entitled "Droplet Actuator Devices and Methods," published on Jan. 6, 2011, the entire disclosure of which is incorporated herein by reference.

One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness of at least about 20 nm, 50 nm, 75 nm, 100 nm or more. Alternatively or additionally the thickness can be at most about 200 nm, 150 nm, 125 nm or less. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.); NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® non-woven aramid reinforcement (available from DuPont, Wilmington, Del.); NOMEX® brand fiber (available from DuPont, Wilmington, Del.); and paper.

Various materials are also suitable for use as the dielectric component of the substrate. Examples include: vapor deposited dielectric, such as PARYLENE™ C (especially on glass), PARYLENE™ N, and PARYLENE™ HT (for high temperature, ~300° C.) (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; polypropylene; and black flexible circuit materials, such as DuPont™ Pyralux® HXC and DuPont™ Kapton® MBC (available from DuPont, Wilmington, Del.).

Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc.

In some cases, a substrate of the present disclosure may be derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, other fluorinated monomers for plasma-enhanced chemical vapor deposition (PECVD), and organosiloxane (e.g., SiOC) for PECVD. Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the methods and apparatus set forth herein includes those described in Meathrel et al., U.S. Pat. No. 7,727,466, entitled "Disintegratable Films for Diagnostic Devices," issued on Jun. 1, 2010, the entire disclosure of which is incorporated herein by reference. Pursuant to various aspects of the invention, detection of particles may be accomplished in droplets on droplet actuators or other microfluidic devices, such as conventional wells, slides, fluidic channels, and other microfluidic chambers.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other.

The terms "splitting," "separating" and "dividing" are not intended to imply any particular outcome with respect to volume of the resulting droplets (e.g., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator."

The term "particle" means naturally occurring and human-made matter, including but not limited to molecules, living and non-living cells, and other small items that may reside within a liquid droplet and/or within a molecule or cell.

Impedance or capacitance sensing or imaging techniques may sometimes be used to determine or confirm the outcome of a droplet operation. Examples of such techniques are described in Sturmer et al., U.S. Patent Pub. No. 20100194408, entitled "Capacitance Detection in a Droplet Actuator," published on Aug. 5, 2010, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec.

In one embodiment, the electrode is operated in AC mode but is switched to DC mode for imaging. It is helpful for conducting droplet operations for the footprint area of droplet to be similar to electrowetting area. In other words, 1×-, 2×- 3×-droplets are usefully controlled operated using 1, 2, and 3 electrodes, respectively. If the droplet footprint is greater than the number of electrodes available for conducting a droplet operation at a given time, the difference between the droplet size and the number of electrodes typically may not be greater than 1. In other words, a 2× droplet is usefully controlled using 1 electrode and a 3× droplet is usefully controlled using 2 electrodes. When droplets include beads, the droplet size may be equal to the number of electrodes controlling the droplet, e.g., transporting the droplet. Pursuant to various aspects of the invention, particles may be detected and/or quantified in one or more droplets prior to, in the process of, or following droplet operations. Further, droplet operations may be adjusted as a result of the detection, e.g., the cut-off step of a dispensing or splitting droplet operation may be completed only when a predetermined number of cells is present in a desired region of the droplet being dispensed or split. For example, a dispensing operation may be completed only when a predetermined number of cells is present in the region being dispensed. As another example, a dispensing operation may be completed only when a single cell is present in the region being dispensed. Subsequent droplet operations may also be conditioned on the detection step. For example, droplet transport destination may be conditioned on the number of particles actually dispensed.

"Filler fluid" means a fluid associated with a droplet operations substrate of a droplet actuator, which fluid is sufficiently immiscible with a droplet phase to render the droplet phase subject to electrode-mediated droplet operations. For example, the droplet operations gap of a droplet actuator is typically filled with a filler fluid. The filler fluid may, for example, be or include a low-viscosity oil, such as silicone oil or hexadecane filler fluid. The filler fluid may be or include a halogenated oil, such as a fluorinated or perfluorinated oil. The filler fluid may fill the entire gap of the droplet actuator or may coat one or more surfaces of the droplet actuator. Filler fluids may be conductive or non-conductive. Filler fluids may be selected to improve droplet operations and/or reduce loss of reagent or target substances from droplets, improve formation of microdroplets, reduce cross contamination between droplets, reduce contamination of droplet actuator surfaces, reduce degradation of droplet actuator materials, etc. For example, filler fluids may be selected for compatibility with droplet actuator materials. As an example, fluorinated filler fluids may be usefully employed with fluorinated surface coatings.

Fluorinated filler fluids are useful to reduce loss of lipophilic compounds, such as umbelliferone substrates like 6-hexadecanoylamido-4-methylumbelliferone substrates (e.g., for use in Krabbe, Niemann-Pick, or other assays); other umbelliferone substrates are described in Winger et al., U.S. Patent Pub. No. 20110118132, entitled "Enzymatic Assays Using Umbelliferone Substrates with Cyclodextrins in Droplets of Oil," published on May 19, 2011, the entire disclosure of which is incorporated herein by reference. Examples of suitable fluorinated oils include those in the Galden line, such as Galden HT170 (bp=170° C., viscosity=1.8 cSt, density=1.77), Galden HT200 (bp=200 C, viscosity=2.4 cSt, d=1.79), Galden HT230 (bp=230 C, viscosity=4.4 cSt, d=1.82) (all from Solvay Solexis); those in the Novec line, such as Novec 7500 (bp=128 C, viscosity=0.8 cSt, d=1.61), Fluorinert FC-40 (bp=155° C., viscosity=1.8 cSt, d=1.85), Fluorinert FC-43 (bp=174° C., viscosity=2.5 cSt, d=1.86) (both from 3M). In general, selection of perfluorinated filler fluids is based on kinematic viscosity (<7 cSt is preferred, but not required), and on boiling point (>150° C. is preferred, but not required, for use in DNA/RNA-based applications (PCR, etc.)).

Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the methods and apparatus set forth herein are provided in Srinivasan et al, International Patent Pub. No. WO/2010/027894, entitled "Droplet Actuators, Modified Fluids and Methods," published on Jun. 3, 2010; Srinivasan et al, International Patent Pub. No. WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Jan. 15, 2009; and Monroe et al., U.S. Patent Pub. No. 20080283414, entitled "Electrowetting Devices," published on Nov. 20, 2008, the entire disclosures of which are incorporated herein by reference, as well as the other patents and patent applications cited herein. Fluorinated oils may in some cases be doped with fluorinated surfactants, e.g., Zonyl FSO-100 (Sigma-Aldrich) and/or others. A filler fluid is typically a liquid. In some embodiments, a filler gas can be used instead of a liquid. Detection of particles pursuant to various embodiments of the invention may be accomplished in a droplet in filler fluid.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads. Detection of particles pursuant to various embodiments of the invention may be accomplished while the particles are immobilized.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, CoO, NiO, $Mn_2O_3$, $Cr_2O_3$, and CoMnP.

"Reservoir" means an enclosure or partial enclosure configured for holding, storing, or supplying liquid. A droplet actuator system of the present disclosure may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or flow path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap. Detection of particles pursuant to certain embodiments of the invention may be accomplished in a reservoir.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface. In one example, filler fluid can be considered as a film between such liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

The terms "fluidics cartridge," "digital fluidics cartridge," "droplet actuator," and "droplet actuator cartridge" as used throughout the description can be synonymous.

DESCRIPTION

Figure 1:
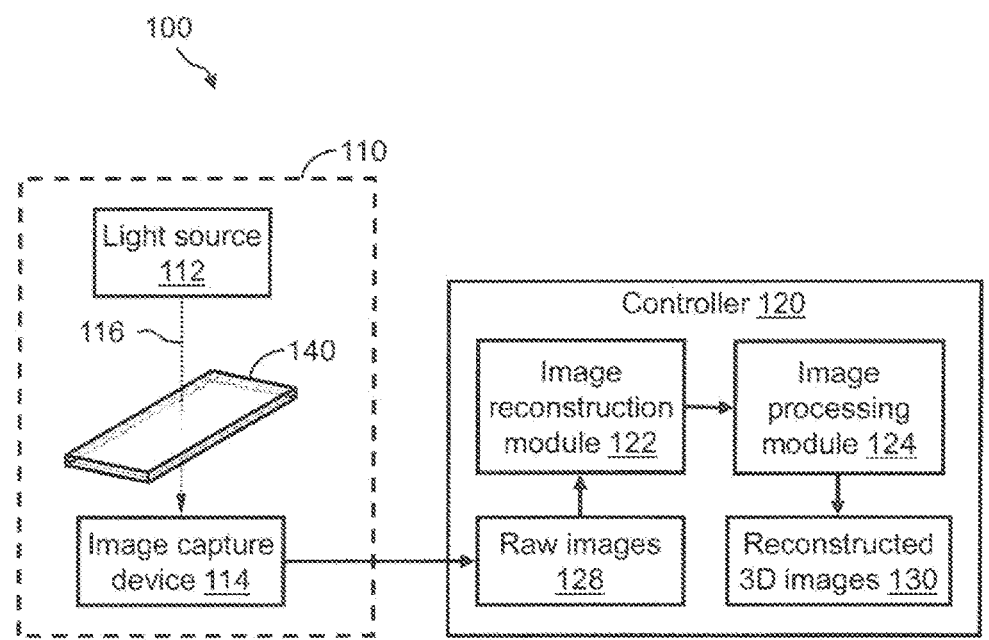
FIG. 1 illustrates a block diagram of an example of a microfluidics system in accordance with embodiments herein.

In accordance with embodiments herein, microfluidics systems and methods are described for identifying and/or tracking particles in a droplet. For example, the particle may be a bead, a cell, or any other type of particle. For example, embodiments herein are useful in distinguishing cells from other particles. The microfluidics systems and methods provide the capability to image a large area (e.g., a few square millimeters) within a digital fluidics chamber using interference microscopy, wherein the image of the interference pattern is acquired, instead of an image of the micrometric object itself. The interference pattern results from the incoming light that interferes with the light scattered by the object. In the case of micrometric objects (e.g., cells, bacteria, etc.), the acquired interference pattern may typically be about 100 µm in diameter so that the area can be imaged using a lens-free imaging configuration or using a low magnification lens.

In accordance with embodiments herein, a microfluidics imaging system is provided that comprises a light source to emit light onto a cartridge illumination zone. The system includes a fluidics cartridge sized and dimensioned to be positioned at the cartridge illumination zone wherein the fluidics cartridge includes top and bottom substrates separated by a droplet operations gap. The droplet gap is configured to retain a filler fluid including at least one sample droplet containing one or more particles of interest. The fluidics cartridge includes droplet operations electrodes arranged along at least one of the top and bottom substrates to control sample droplet manipulation when activation and deactivated.

Alternatively, the image capture device is held in a predetermined relation relative to the light source and cartridge illumination zone such that the fluidics cartridge is located at an intermediate point along a path of the light between the light source and the image capture device. The image capture device captures a raw two-dimensional (2-D) image containing a particle diffraction pattern corresponding to one or more particles of interest. The system includes one or more processors operably coupled to the image capture device. The one or more processors are configured to perform image reconstruction on the raw 2-D image to generate a reconstructed image to be utilized in connection with at least one of identifying and tracking the one or more particles of interest.

In accordance with embodiments herein, a lens free optical detector is provided that comprises a cartridge illumination zone configured to receive a fluidics cartridge having top and bottom substrates separated by a droplet operations gap that retains a filler fluid including at least one sample droplet containing one or more particles of interest. The fluidics cartridge includes droplet operations electrodes arranged along at least one of the top and bottom substrates to control sample droplet manipulation when activated and deactivated.

Alternatively, the system includes a light source that emits light onto the cartridge illumination zone. The image capture device is held in a predetermined relation relative to the light source and cartridge illumination zone such that the fluidics cartridge is located at an intermediate point along a path of the light between the light source and the image capture device. The image capture device may capture a raw two-dimensional (2-D) image containing a particle diffraction pattern corresponding to the one or more particles of interest.

In accordance with embodiments herein, a method for performing microfluidics imaging that comprises positioning a fluidics cartridge at a cartridge illumination zone. The fluidics cartridge includes top and bottom substrates separated by a droplet operations gap. The droplet operations gab is configured to retain a filler fluid including at least one sample droplet containing one or more particles of interest. The fluidics cartridge includes droplet operations electrodes arranged along at least one of the top and bottom substrates to control sample droplet manipulation when activated and deactivated.

Alternatively, the method comprises emitting light onto the cartridge illumination zone. The method further comprises capturing a raw two-dimensional (2-D) image containing a particle diffraction pattern corresponding to the one or more particles of interest utilizing an image capture device that is held in a predetermined relation relative to the light source and cartridge illumination zone such that the fluidics cartridge is located at an intermediate point along a path of the light between the light source and the image capture device. The method utilizes one or more processors to perform image reconstruction on the raw 2-D image to generate a reconstructed image to be utilized in connection with at least one of identifying and tracking the one or more particles of interest.

In some embodiments, the microfluidics system may include a diffraction-based lens-free optical detector and a controller for identifying and/or tracking particles in a droplet, wherein the diffraction-based lens-free optical detector operates in transmission mode. The diffraction-based lens-free optical detector includes a light source and an image capture device. In the lens-free imaging configuration, a substantially transparent fluidics cartridge holding the sample liquid is arranged between the light source and the image capture device. Further, the microfluidics system may include certain software modules for processing the images from the diffraction-based lens-free optical detector. For example, an image reconstruction receives a 2-D image of a diffraction pattern from the image capture device and based thereon then generates a high quality 3-D image of particles in the sample liquid. The image reconstruction process may avoid z-scanning that is required using conventional microscopy.

In other embodiments, the microfluidics system includes a reflection interference microscopy configuration that can be used with a non-transparent fluidics cartridge. Namely, the microfluidics system includes a controller and a reflection interference-based optical detector that includes a low magnification lens.

Embodiments of the microfluidics system may include certain software modules, such as the image reconstruction process, for processing the 2-D images from the reflection interference-based optical detector and generating 3-D images. Again, the image reconstruction process may avoid z-scanning that is required using conventional microscopy.

An aspect of the presently disclosed microfluidics systems and methods is to omit z-scanning, thereby affording fast time-lapse acquisition. Accordingly, a video can be captured of the sample droplet during any type of droplet operation, wherein the particles in the sample droplet can be identified and tracked throughout the movement of the sample droplet.

Another aspect of the presently disclosed microfluidics systems and methods is to be used with single cell technology, such as when determining the genetic information of a single cell. For example, using the presently disclosed microfluidics systems and methods, a droplet containing a single cell can be transported into any downstream process, such as an assay.

FIG. 1 illustrates a block diagram of a microfluidics system 100 formed in accordance with embodiments herein. The microfluidics system 100 includes a diffraction-based lens-free optical detector 110 for identifying and/or tracking particles in a droplet within a fluidics cartridge. The diffraction-based lens-free optical detector 110 may operate in a transmission mode. Diffraction-based lens-free optical detector 110 includes a light source 112 and an image capture device 114. Light source 112 emits light 116 that is directed toward image capture device 114. In one example, light source 112 is a light-emitting diode (LED), such as a green LED.

Image capture device 114 may be a two dimensional (2-D) image sensor, e.g., in a plane perpendicular to the illumination direction Z. Image capture device 114 may be a pixelated image sensor, such as a complementary metal-oxide semiconductor (CMOS) sensor or a charge-coupled device (CCD) sensor. In one example, image capture device 114 can be a CMOS sensor mounted on a printed circuit board (PCB). The image capture device 114 may capture a raw two-dimensional (2-D) image containing a particle diffraction pattern corresponding to the one or more particles of interest. Optionally, the image capture device 114 obtains multiple raw 2-D images and one or more processors are configured to perform at least one of i) sample particle identification and ii) sample particle tracking between the multiple raw 2-D images.

Microfluidics system 100 also includes a controller 120, having one or more processors, for processing information from diffraction-based lens-free optical detector 110. Controller 120 may be, for example, a general purpose computer, special purpose computer, personal computer, or other programmable data processing apparatus. Controller 120 may include the processor structure, memory and other electronic components described in one or more of the patents or publications incorporated herein by reference that relate to microfluidics. Controller 120 includes memory (or is coupled to memory) that stores, among other things, raw 2D images, reconstructed 3-D images, and program instructions that are executed by one or more processors to perform the operations described herein. Controller 120 serves to provide processing capabilities, such as storing, interpreting, and/or executing software instructions, as well as controlling the overall operation of microfluidics system 100. Controller 120 may be configured and programmed to control data and/or power aspects of any components of microfluidics system 100. The controller includes one or more processors configured to perform image reconstruction on the raw 2-D image to generate a reconstructed image to be utilized in connection with at least one of the identifying and tracking the one or more particles of interest. Further, an image reconstruction module 122 as well as one or more other image processing module 124 resides at controller 120. Image reconstruction module 122 and image processing module 124 can be implemented in software or hardware. Any image capture event of image capture device 114 produces a raw image 128 that is transmitted to controller 120 and saved in memory that is included within or coupled to the controller 120. Image reconstruction module 122 and image processing modules 124 are used to process the raw images 128 and based thereon, generate reconstructed 3-D images 130. The 3-D images 130 are saved in memory that is included within or coupled to the controller 120. Reconstructed 3-D images 130 are analyzed by the image processing module 124 for identifying and/or tracking particles in a droplet. More details of using image reconstruction module 122 and image processing modules 124 for identifying and/or tracking particles in a droplet are shown and described hereinbelow, such as with reference to FIG. 6 through FIG. 14C.

In one example, diffraction-based lens-free optical detector 110 may be used in combination with a substantially transparent fluidics cartridge, such as a transparent fluidics cartridge 140. More details of transparent fluidics cartridge 140 are shown and described hereinbelow with reference to FIG. 2A and FIG. 2B. For example, FIG. 1 shows transparent fluidics cartridge 140 arranged between light source 112 and image capture device 114 and in the path of light 116. Namely, because transparent fluidics cartridge 140 is substantially transparent, light 116 can pass through transparent fluidics cartridge 140 and impinge on image capture device 114. More details of diffraction-based lens-free optical detector 110 in relation to transparent fluidics cartridge 140 are shown and described hereinbelow with reference to FIG. 3.

Figure 2A:
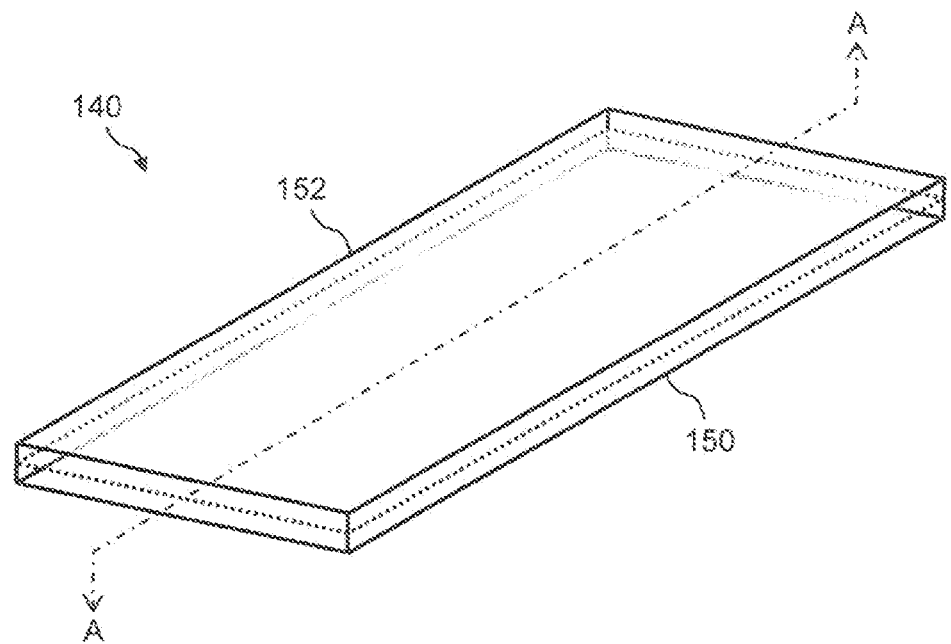
FIG. 2A illustrates a perspective view of an example of a substantially transparent fluidics cartridge in accordance with embodiments herein.
Figure 2B:
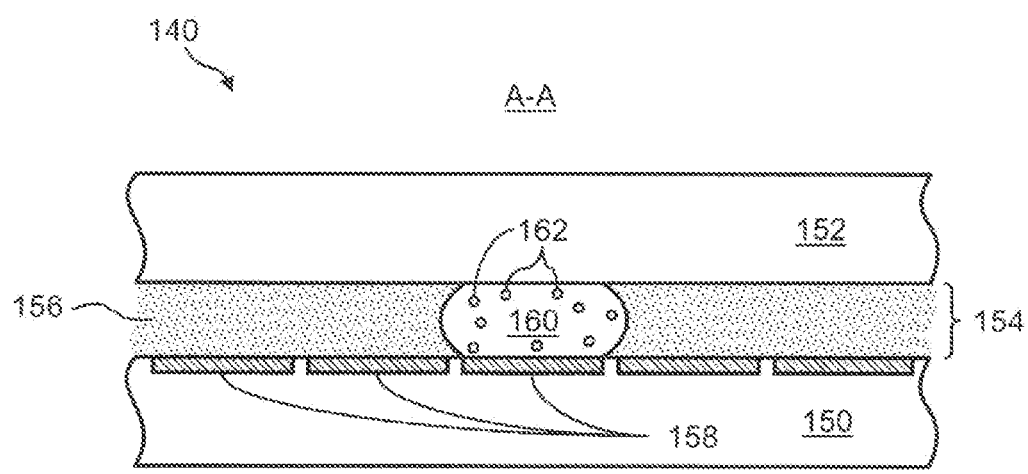
FIG. 2B illustrates a cross-sectional view of a portion of the substantially transparent fluidics cartridge shown in FIG. 2A taken along line A-A.

FIG. 2A illustrates a perspective view of an example of the fluidics cartridge 140 that is substantially transparent. The fluidics cartridge 140 is sized and dimensioned to be positioned at the cartridge illumination zone. FIG. 2B illustrates a cross-sectional view of a portion of fluidics cartridge 140 taken along line A-A of FIG. 2A. Fluidics cartridge 140 includes a bottom substrate 150 and a top substrate 152 that are separated by a droplet operations gap 154. Droplet operations gap 154 contains filler fluid 156. The filler fluid 156 is, for example, low-viscosity oil, such as silicone oil or hexadecane filler fluid. Bottom substrate 150 may include an arrangement of droplet operations electrodes 158 (e.g., electrowetting electrodes). Top substrate 152 may include a ground reference plane or electrode (not shown). Droplet operations are conducted atop droplet operations electrodes 158 on a droplet operations surface. For example, FIG. 2B shows a droplet 160 in droplet operations gap 154 and atop one of the droplet operations electrodes 158. With respect to fluidics cartridge 140, controller 120 or any other controller (not shown) may be used to control droplet manipulation by activating/deactivating droplet operations electrodes 158.

Droplet 160 can be, for example, any aqueous droplet, such as sample droplet. Additionally, one or more particles 162 may be present in droplet 160. The one or more particles 162 may be any type of micrometric objects to be processed in a fluidics cartridge. The particles 162 in a given droplet 160 can be the same or different types of particles. One type of particle 162 is a magnetically responsive bead. Another type of particle 162 is a cell from any living organism, such as any type of human cell, animal cell, or plant cell. Yet another type of particle 162 is bacteria.

Bottom substrate 150, top substrate 152, droplet operations electrodes 158, and the ground reference plane or electrode (not shown) are formed of materials that are substantially transparent to light, such as to light 116 emitted from light source 112. In one example, bottom substrate 150 and top substrate 152 are formed of glass or plastic, while droplet operations electrodes 158 and the ground reference plane or electrode (not shown) are formed of indium tin oxide (ITO). ITO is an electrically conductive, substantially transparent material. Accordingly, light may pass substantially unobstructed through fluidics cartridge 140. For example, light may enter top substrate 152 and exit bottom substrate 150, as shown and described hereinbelow with reference to FIG. 3.

Figure 3:
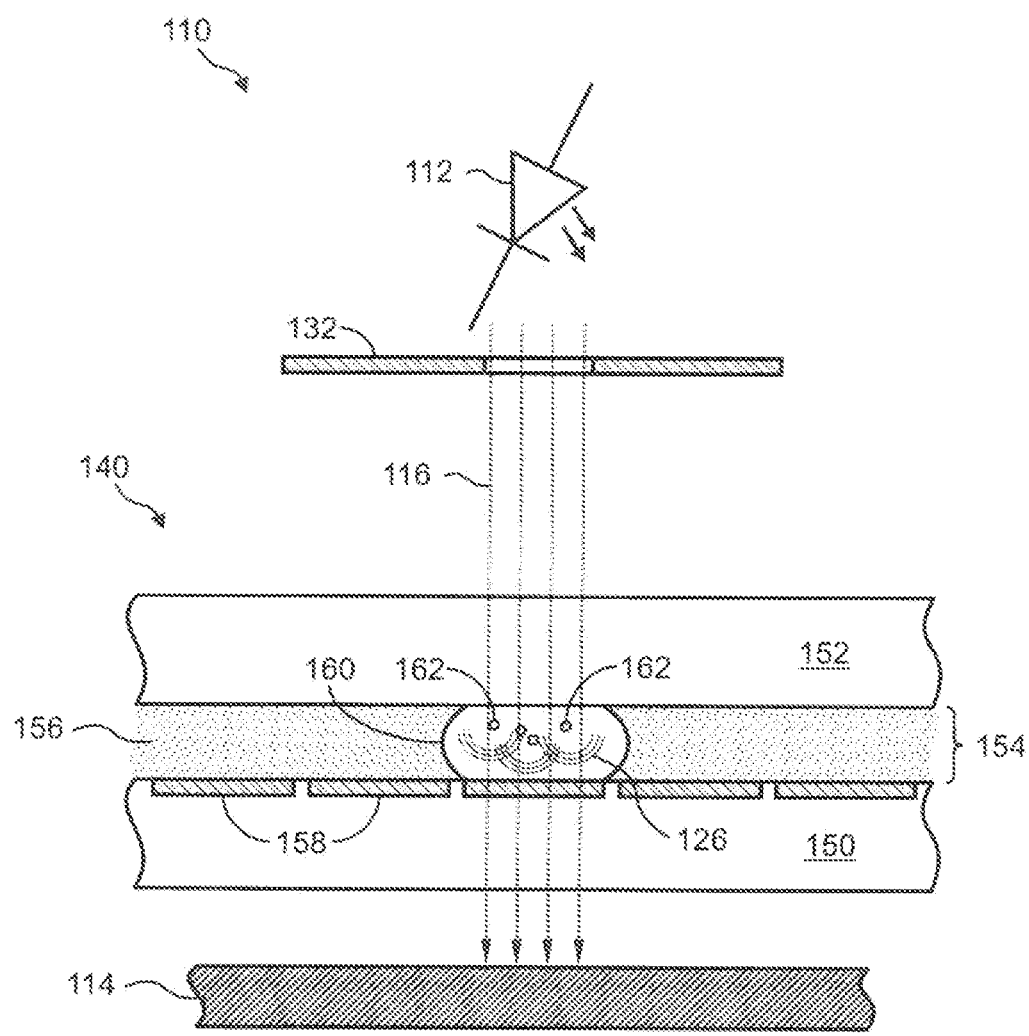
FIG. 3 illustrates a diffraction-based lens-free optical detector of the microfluidics system of FIG. 1 in accordance with embodiments herein.

FIG. 3 illustrates more details of diffraction-based lens-free optical detector 110 of microfluidics system 100 of FIG. 1, such as when in use with transparent fluidics cartridge 140 of FIG. 2A and FIG. 2B. Diffraction-based lens-free optical detector 110 operates in a transmission mode, such that any light 116 emitted from light source 112 is able to pass through the structure of fluidics cartridge 140 and reach image capture device 114. The diffraction-based lens-free optical detector 110 includes a spatial filter 132 that may be positioned in a select relation to light source 112. Spatial filter 132 may represent, for example, a plate that has a 150-micrometers pinhole therein. The 150-micrometers pinhole is essentially a circular aperture for directing light 116 toward fluidics cartridge 140 and image capture device 114. Optionally, the spatial filter 132 may utilize other types of apertures, other than circular apertures (e.g., a slit shaped aperture). In one embodiment, a single aperture may be aligned with each cartridge illumination zone. Optionally, more than one aperture may be aligned with each cartridge illumination zone. For example, a single image capture device (or an array of closely positioned image capture devices) may be configured to process multiple droplets in parallel. A fluidics cartridge may include multiple cartridge illumination zones or a large cartridge illumination zone configured to permit parallel processing of multiple droplets located at separate corresponding electrodes in the fluidics cartridge. When a fluidics cartridge is shaped and dimensioned to permit parallel imaging of multiple droplets, the cartridge illumination zone may include at least one aperture aligned with each section of the fluidics cartridge that is configured to be illuminated and imaged.

The image capture device 114 is held in a predetermined relation relative to the light source 112 and cartridge illumination zone such that the fluidics cartridge 140 is located at an intermediate point along a path of the light between the light source 112 and the image capture device 114. The image capture device 114 captures a raw two-dimensional image containing a particle diffraction pattern corresponding to one or more particles of interest. Image capture device 114 may be positioned a select distance away from droplet 160 (e.g., from about 1 mm to about 1 cm). Optionally, the distance may be about 1 mm away from droplet 160. The field of view (FOV) of image capture device 114 is large enough to capture an image of droplet 160 in its entirety with just one capture event. The image capture device 114 is sized to capture the raw 2-D image in a single capture event to form an image data set at a select point in time for the entire droplet 160 and optionally for the entire fluidics cartridge 140. The FOV of image capture device 114 can be, for example, about 24 mm$^2$ or about 30 mm$^2$.

In operation, when light 116 passes through droplet 160 that contains particles 162, the light diffracts off of particles 162. Accordingly, it is diffracted light that reaches image capture device 114. Namely, image capture device 114 captures an image of the diffraction pattern of droplet 160 and particles 162 (and any features of transparent fluidics cartridge 140). The image capture device 114 is maintained in a fixed position and orientation such that fluidics cartridge 140 is positioned between the light source 112 and image capture device 116 with the light passing along an illumination direction through the fluidics cartridge before impinging upon the image capture device. For example, FIG. 3 shows diffraction rings 126 that correspond to particles 162 in droplet 160.

Figure 4:
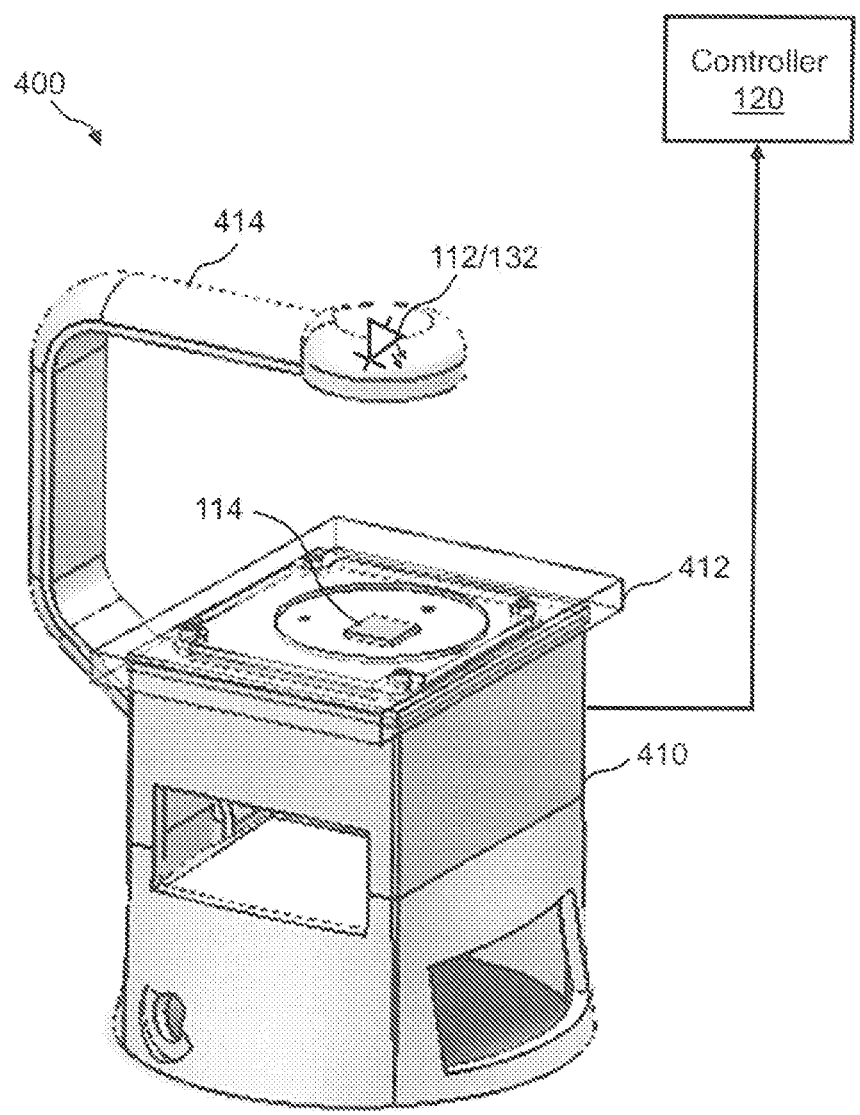
FIG. 4 and FIG. 5 illustrate perspective views of one example of the physical instantiation of the microfluidics system of FIG. 1 in accordance with embodiments herein.
Figure 5:
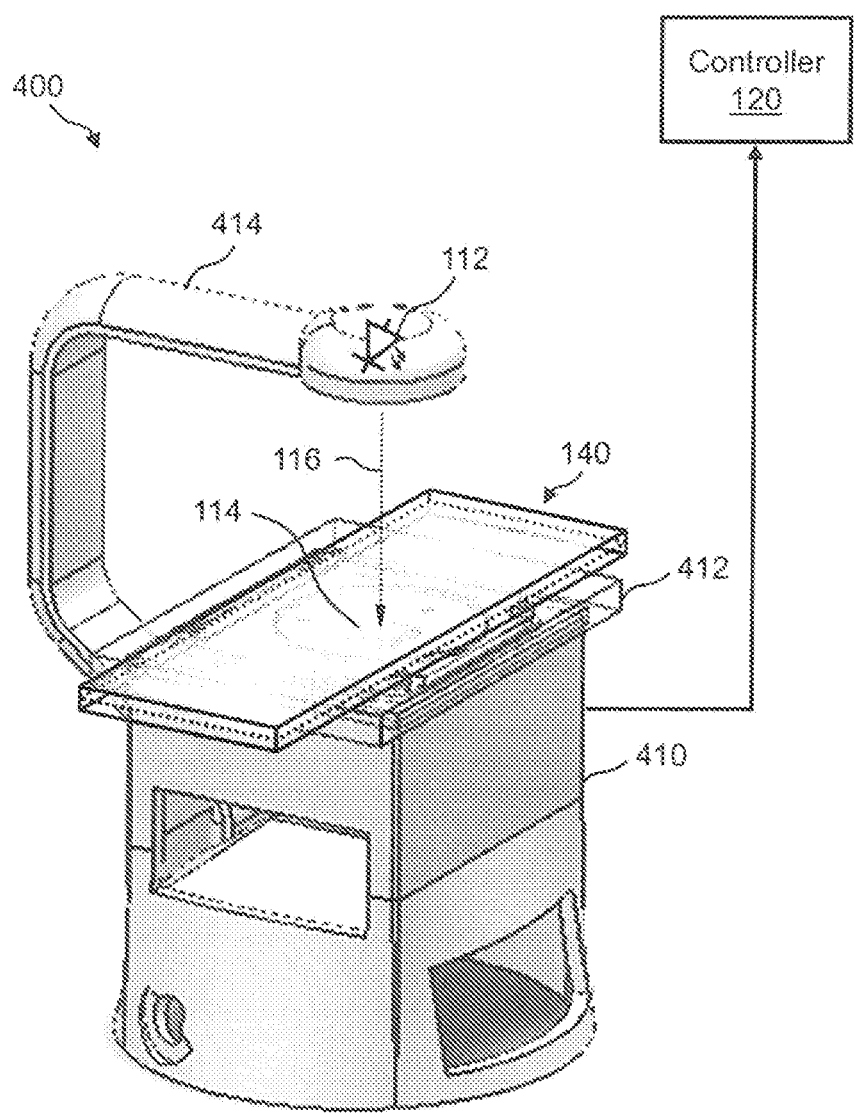

FIG. 4 and FIG. 5 illustrate perspective views of a detector assembly 400, which is one example of the physical instantiation of diffraction-based lens-free optical detector 110 of microfluidics system 100 of FIG. 1. In this example, detector assembly 400 includes a base 410. A platform 412 holds the fluidics cartridge 140 (e.g., transparent fluidics cartridge 140) and sits atop base 410. The base 410 defines a cartridge illumination zone. The fluidics cartridge 140 is sized and dimensional to be positioned at the cartridge illumination zone. FIG. 4 shows detector assembly 400 absent the fluidics cartridge, while FIG. 5 shows detector assembly 400 holding transparent fluidics cartridge 140 atop platform 412. Detector assembly 400 also includes an arm 414 for holding light source 112 and spatial filter 132 above platform 412 and in a select relation to the platform 412 and fluidics cartridge 140. Image capture device 114 is provided at a select position and relation to platform 412 such that the image capture device 114 sits below the fluidics cartridge 140. FIG. 5 shows light 116 from light source 112 passing through transparent fluidics cartridge 140 and impinging on image capture device 114. The image capture device 114 is positioned at a select location relative to a reference point on the platform 412 such that the image capture device 114 is aligned with the fluidics cartridge 140 and light 116. Image capture device 114 in detector assembly 400 is electrically connected to controller 120. Other components (not shown) and/or subsystems (not shown) may be installed in base 410. For example, heating/cooling mechanisms may be installed in base 410.

An aspect of detector assembly 400 is that light source 112, image capture device 114, and controller 120 can be implemented at very low cost compared with conventional microscopy systems. An example of a low cost controller is shown hereinbelow with reference to FIG. 19.

Figure 6:
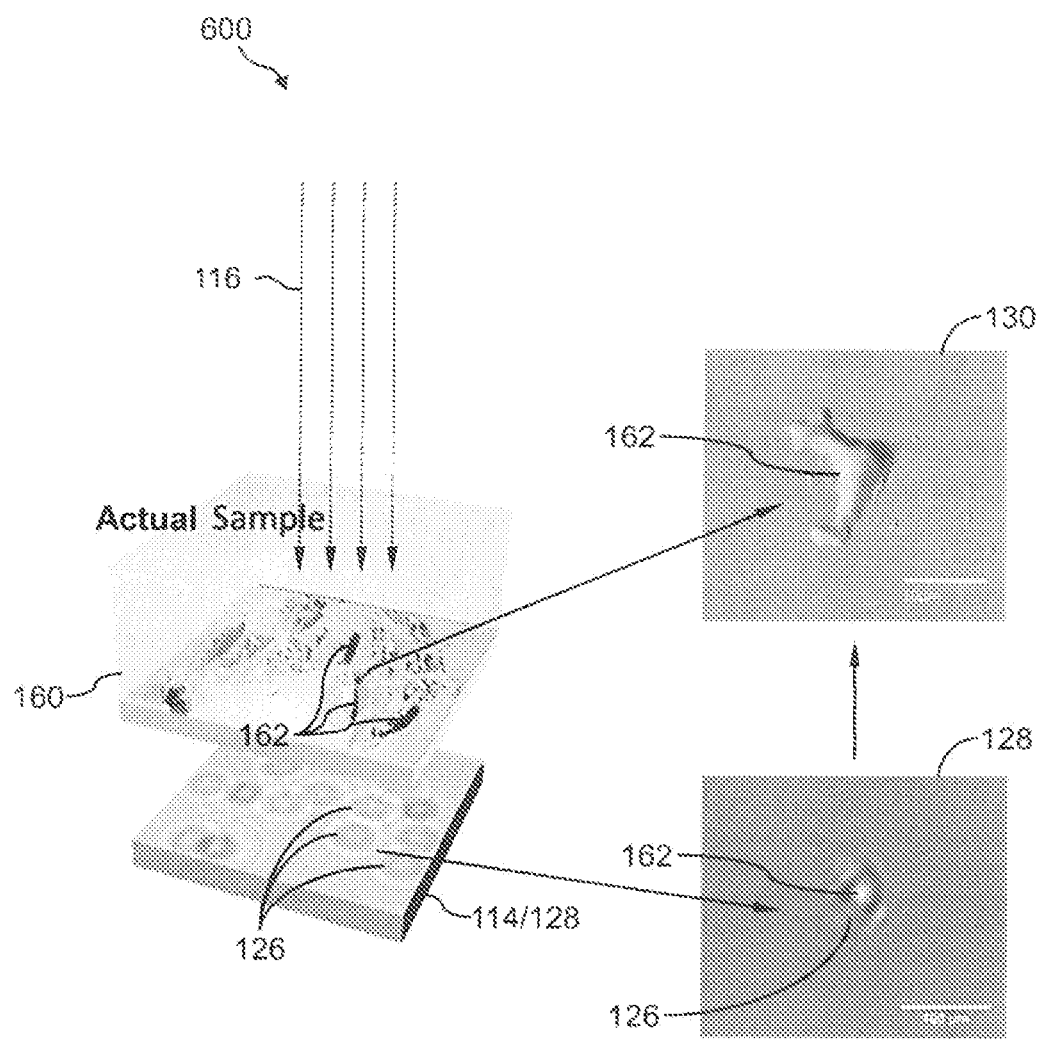
FIG. 6 illustrates a pictorial representation of an example of a process of using the microfluidics system of FIG. 1 to identify and/or track particles in a droplet, in accordance with embodiments herein.

FIG. 6 shows a pictorial representation of an example of a process 600 of using microfluidics system 100 of FIG. 1 to identify and/or track particles in a droplet. In process 600, the sample droplet 160 is illuminated with light 116 from light source 112. FIG. 6 shows the actual sample droplet 160 that contains cells and particles 162. Namely, FIG. 6 shows the sample droplet 160 in the context of the FOV of image capture device 114. Next, image capture device 114 is used to capture a raw image 128 of the sample droplet 160. For example, FIG. 6 shows the raw image 128, again in the context of the FOV of image capture device 114. Captured in the raw image 128 is the diffraction pattern of the sample droplet 160. As light 116 intersects the sample droplet 160, each particle 162 creates a corresponding component or "local" diffraction pattern (e.g., cell-related or particle-related diffraction pattern). The nature of the local diffraction pattern associated with each particle is dependent on various characteristics of the associated particle. For example, the characteristics that impact a diffraction pattern may include particle diameter, three-dimensional structure, transparency, type of material (e.g., water based, polymer based), living state (e.g., alive, dead, partially alive, partially dead) and the like. As a further example, when the particle is a living cell that is semi-transparent and has a predetermined diameter, the cell may generate a corresponding component or "local" cell-related diffraction pattern. Diffraction patterns may be characterized based on various criteria, such as a shape of the waves, whether the waves achieve a select amplitude, the peak to peak amplitude of the waves, the frequency of the waves, the phase of the waves, etc. In the example of FIG. 6, the diffraction patterns are circular as a circular (pinhole) aperture is used in the spatial filter, however other shapes of diffraction patterns may result when other types of apertures are used. For example, a slit type aperture may produce a semi-circular wave-front that results in local semi-circular diffraction patterns created by each particle.

When a droplet includes more than one particle, the local diffraction patterns associated with the particles combine to form a composite diffraction pattern. The composite diffraction pattern includes component diffraction patterns associated with individual cells, particles or other structures in the sample droplet 160. For example, raw image 128 shows the diffractions rings 126 that correspond to particles 162 in the sample droplet 160. The diffraction rings 126 include component diffraction patterns associated with corresponding particles 162, where the diffraction rings 126 represent a composite diffraction pattern as each individual set of diffraction rings 126 has been impacted/altered by intersecting diffraction rings 126 originating from other particles in the droplet. The raw 2-D image contains a plurality of separate and distinct particle diffraction patterns correspond to associated particles of interest. FIG. 6 also shows an exploded view of one diffraction ring 126/particle 162 in the raw image 128 from image capture device 114. Next, the raw image 128 is processed using image reconstruction module 122 and image processing modules 124 to generate a reconstructed 3-D image 130 of the sample droplet 160. The reconstruction 3-D image has at least one image component corresponding to the particle of interest. By way of example, FIG. 6 shows an exploded view of one particle 162 in reconstructed 3-D image 130.

An aspect of microfluidics system 100 is that, using diffraction-based lens-free optical detector 110, the reconstructed 3-D image 130 may be created from a single 2-D image capture event (e.g., one raw image 128, which is a 2-D image). For example, image reconstruction module 122 and image processing modules 124 may process only one raw image 128 to create the corresponding reconstructed 3-D image 130. The 3-D image 130 may be represented in various manners. By way of example, the 3-D image 130 may be presented as a gray scale image where an intensity or shading of each voxel is representative of a physical characteristic of interest from the particle. For example, the gray scale shading of an individual particle in the 3-D image 130 may be defined to represent a height of the particle at the voxel location. The voxel values are defined from the reconstruction based on the composite diffraction pattern as explained herein. The microfluidics system 100 reduces, or entirely eliminates, the need for complex and costly scanning equipment. Further, the time it takes to generate a high quality image of the sample is greatly reduced as compared with conventional microscopy systems.

Referring again to FIG. 1 through FIG. 6, image reconstruction module 122 is used to process raw images 128, wherein each raw image 128 is a 2-D image of a diffraction pattern corresponding to how the particles in the sample liquid diffract the light. That is, the input to image reconstruction module 122 is a 2-D image of the diffraction pattern, while the output of image reconstruction module 122 is a reconstructed 3-D image (e.g., reconstructed 3-D image 130) for example created using a holographic reconstruction process. The image reconstruction module 122 performs z-plane independent reconstruction by using a numerical process to reconstruct the image at different focalization planes. The reconstruction is z-plane independent as the reconstruction avoids z-plane scanning during reconstruction. The z-plane corresponds to the illumination direction in which the light emits from the light source and/or impinges on image capture device. For example, reconstructed 3-D images 130 may be generated from the 2-D raw images 128 using a numerical process according to the Equation 1 below.

$$I \otimes h_{-z} \approx -a - a^* \otimes h_{-2z} \qquad \text{(Equation 1)}$$

$$h_{-z} = -\frac{i}{\lambda z} e^{i\pi \frac{x^2+y^2}{\lambda z}}$$

By way of example, the operation of image reconstruction module 122 can be based, for example, on Allier et al., U.S. Patent Pub. No. 20140248713, entitled "Method for Observing at Least One Object, Such as a Biological Entity, and Imaging System Associated Therewith," published on Sep. 4, 2014; Allier et al., U.S. Patent Pub. No. 20140016137, entitled "Method and System for Reconstructing Optical Properties of Diffracting Objects Immersed in a Liquid Medium," published on Jan. 16, 2014; Poher et al., U.S. Patent Pub. No. 20130323757, entitled "Method and System for Characterizing the Movement Speed of Particles Contained in a Liquid, such as Blood Particles," published on Dec. 5, 2013; Allier, U.S. Pat. No. 8,605,265, entitled "Optical detection process for detecting micron-sized objects in solution," issued on Dec. 10, 2013; and any combinations thereof; the entire disclosures of which are incorporated herein by reference.

The image reconstruction module 122 creates a first true (or base) image of the sample and particles, corresponding to reconstructed 3-D images 130. Optionally, additional image processing may be performed upon the first base image to further enhance the clarity/quality of the image. The additional processing may be performed using one or more other image processing modules 124. In one example, image processing modules 124 may be used to increase the signal-to-noise (S/N) ratio of the first base image to create a filtered image.

Figure 7A:
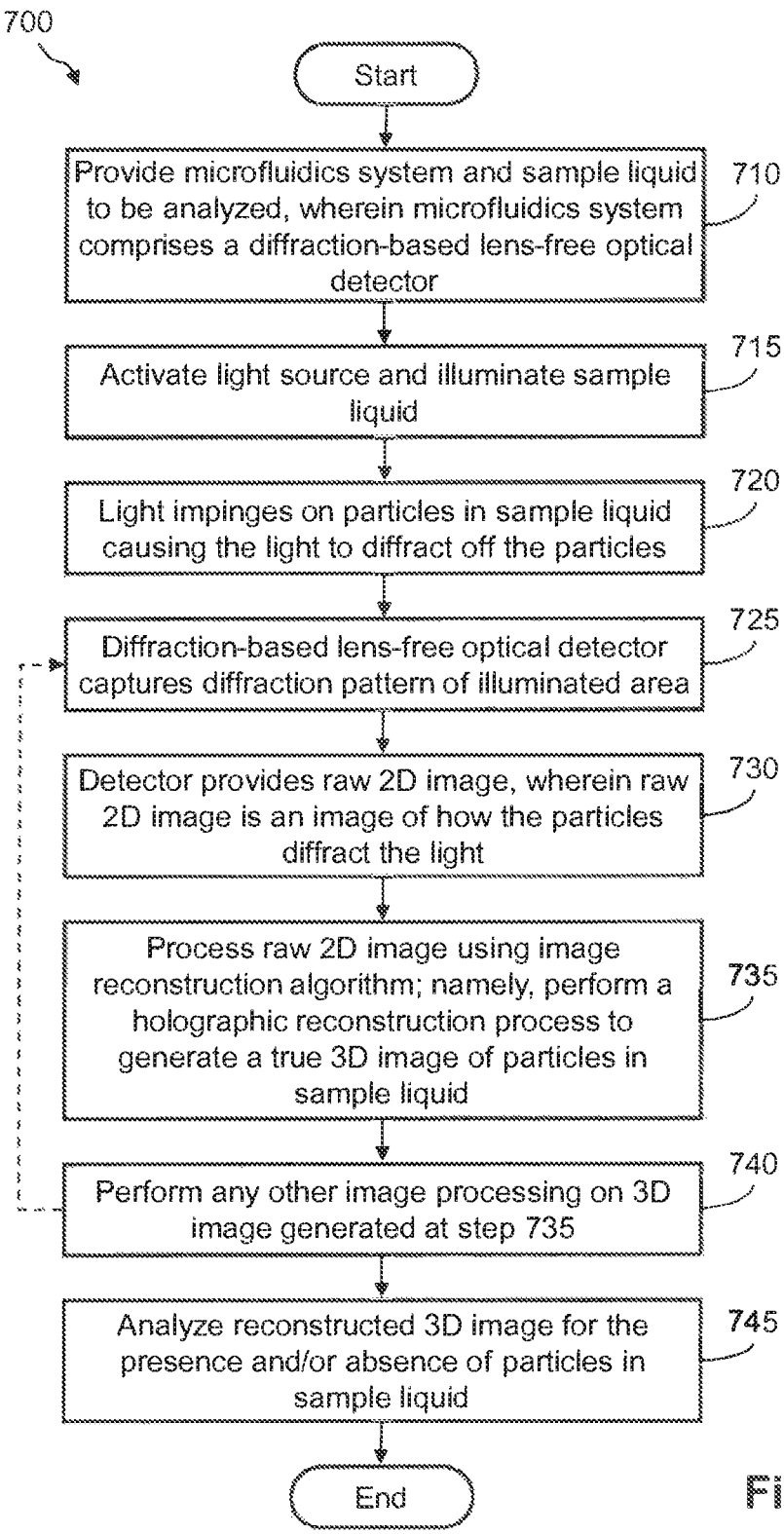
FIG. 7A illustrates a flow diagram for an example of a method of using the microfluidics system of FIG. 1 to identify and/or track particles in a droplet, in accordance with embodiments herein.

FIG. 7A illustrates a flow diagram an example of a method 700 to identify and/or track particles in a droplet. Method 700 may include, but is not limited to, the following operations. At 710, microfluidics system 100 that includes diffraction-based lens-free optical detector 110 is provided. A substantially transparent fluidics cartridge, such as transparent fluidics cartridge 140, that contains the sample liquid to be analyzed is also provided and loaded on the detector 110.

At 715, the light source is activated and the sample liquid is illuminated. For example, light source 112 is activated. In doing so, the sample liquid, such as sample droplet 160, is illuminated.

At 720, the light impinges on the particles in the sample liquid, which causes the light to diffract off the particles. For example, light 116 from light source 112 impinges on particles 162 in sample droplet 160, which causes light 116 to diffract off particles 162.

At 725, the diffraction-based lens-free optical detector captures the diffraction pattern of the illuminated area in at least one frame. For example, image capture device 114 of diffraction-based lens-free optical detector 110 may captures a single image frame of the diffraction pattern of sample droplet 160 that contains particles 162. The diffraction pattern includes diffraction rings 126 that correspond to particles 162.

At 730, the diffraction-based lens-free optical detector provides a raw 2-D image, wherein the raw 2-D image representative of the particle diffraction pattern of light. The raw 2-D image is stored in memory. For example, diffraction-based lens-free optical detector 110 generates a raw image 128, wherein the raw image 128 is an image of how particles 162 diffract light 116. The Raw 2-D image may represent a single frame of digital data captured by the image capture device 114. The raw image 128 is then passed to image reconstruction module 122 at controller 120.

At 735, the raw 2-D image (e.g., raw image 128) is processed using image reconstruction module 122. The image reconstruction module 122 includes one or more processors performing program instructions stored in memory. For example, the image reconstruction module 122 may use a holographic reconstruction process according to, for example, Equation 1 above to generate a reconstructed 3-D image 130. The reconstructed 3-D image represents a first base or true 3-D image of particles 162 in sample droplet 160. The reconstructed 3-D image 130 is then passed to image processing modules 124 at controller 120.

At 740, the image processing modules 124, performs other image processing operations on the reconstructed 3-D image 130 generated at step 735, wherein the other image processing operations are used for further enhancement of reconstructed 3-D image 130 such as to form a second filtered 3-D image. The image processing module 124 includes one or more processors performing program instructions stored in memory.

At 745, the reconstructed 3-D image 130 generated at step 740 is analyzed for the presence (and number) and/or absence of particles 162 in sample droplet 160. In one example, a person visually views the reconstructed 3-D image 130 and determines the presence (and number) and/or absence of particles 162 in sample droplet 160. In another example, the controller 120 may implement a software program to automatically analyze the image data of the reconstructed 3-D image 130 and determine the presence (and number) and/or absence of particles 162 in sample droplet 160.

In method 700, because only one raw image 128 is needed to generate one reconstructed 3-D image 130, method steps 725 through 740 can be repeated in rapid fashion to generate a video of sample droplet 160 that contains particles 162. In one example, in method step 725, image capture device 114 is programmed to capture two frames per second for a period of time (e.g., 5 or 10 secs). In so doing, a video can be captured of the sample droplet 160 during any types of droplet operations, wherein particles 162 in the sample droplet 160 can be identified and tracked throughout the movement of the sample droplet 160.

Figure 7B:
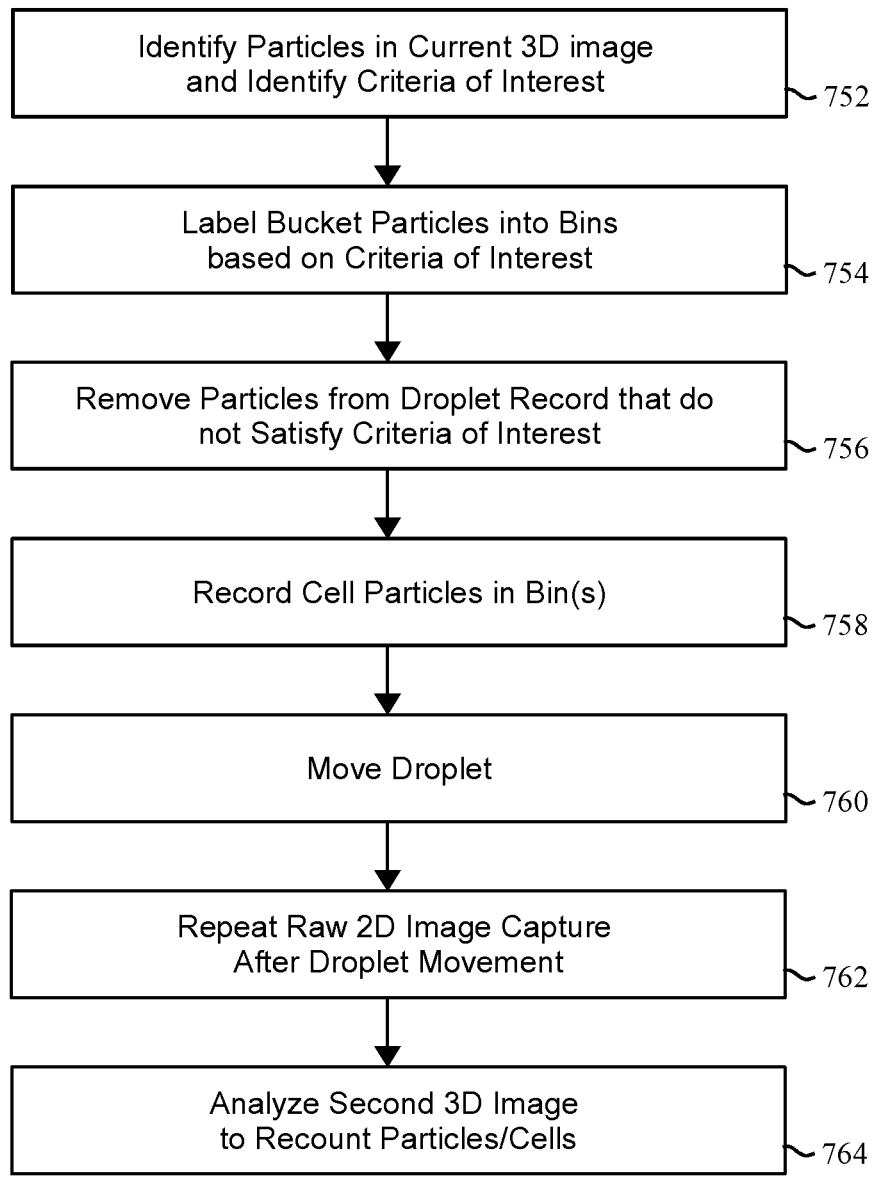
FIG. 7B illustrates a flow diagram for an example of a method for analyzing reconstructed 3-D images to count particles in accordance with embodiments herein.
Figure 7C:
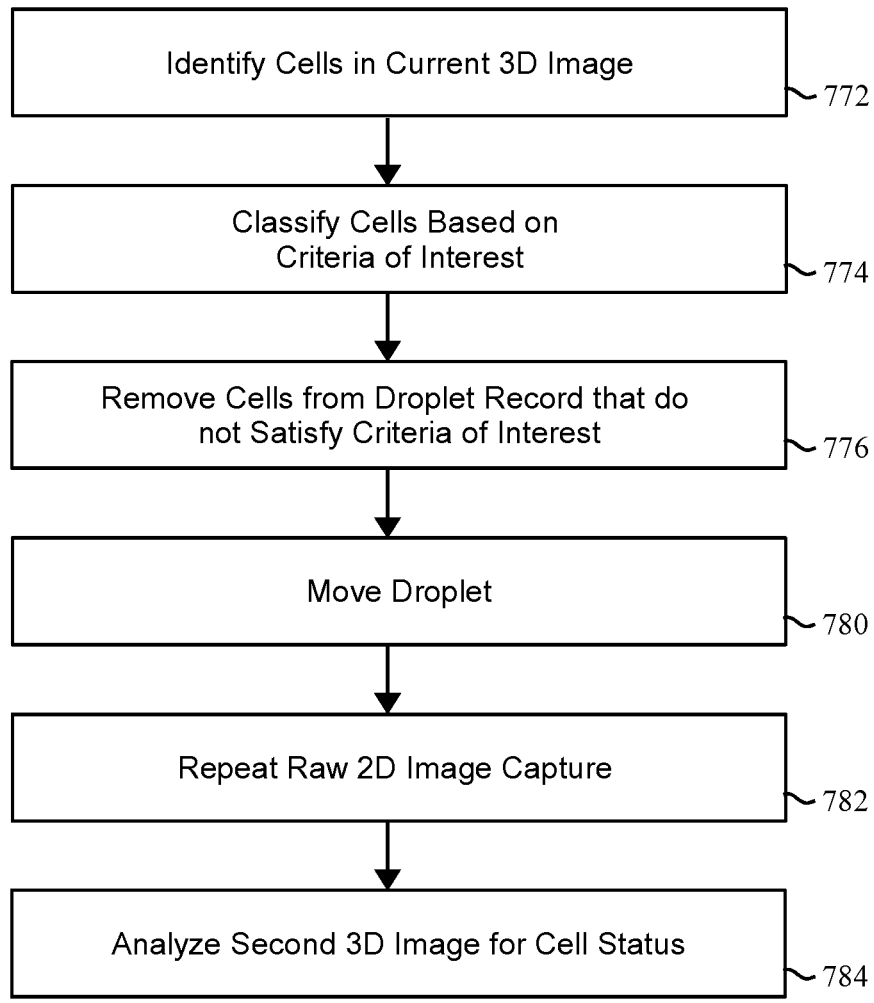
FIG. 7C illustrates a flow diagram for an example of a method for analyzing reconstructed 3-D images to track cells in accordance with embodiments herein.

It should be recognized that the discussion in connection with FIGS. 7A-7C is provided generally in terms of any particle. As a more specific example, the same processes and operations may be utilized in connection cells. As a further example, a cell may include one or more particles, or the cell may be smaller than, the same size as or larger than a particle that is present in a droplet.

FIG. 7B illustrates a flow diagram of a method for analyzing reconstructed 3-D images to count particles in accordance with embodiments herein. The operations of FIG. 7B are performed during the analyzing operation 745 of FIG. 7A. At 752, the image processing module 124 identifies each particle 162 in a current 3-D image 130 and identifies a criteria of interest (e.g., size) associated with each particle 162. The image processing module 124 may form a droplet record based on the identified particles and criteria of interest. As one example, the droplet record may simply include a list of particle sizes (e.g., size xx, size yy, etc.). As one example, the droplet record may simply include a running list of particles with a corresponding size (e.g., particle #1—size xx, particle #2—size yy, etc.). As another example, each particle may be individually and unique identified on the droplet record in order to be subsequently tracked and/or counted (e.g., particle ID1—size xx, particle ID1—size yy, etc.).

At 754, the image processing module 124 groups or buckets the particles 162, from the droplet record, into bins based on the criteria of interest (e.g., particle size). For example, one or more bins may be assigned cut-off sizes that are defined based on particle size(s) of interest. For example, bin size cut-offs may be defined such as 1-10μ, 10-50μ, over 50μ, etc. A particle of interest may have a size between 10μ and 50μ, where particles smaller than 10μ may correspond to foreign material in a droplet or dust on the detector or other material on the substrate, while particles larger than 50μ may be too large to represent the particle of interest.

At 756, the image processing module 124 analyzes the bins in the droplet record and discards or otherwise removes certain particles from further consideration that do not satisfy the criteria of interest. For example, the image processing module 124 may remove, from the droplet record, particles that have a size that is smaller than a predetermined lower threshold. As a further example, the image processing module 124 may remove, from the droplet record, particles that have a size that is greater than a predetermined upper threshold. Additionally or alternatively, the image processing module 124 may remove, from the droplet record, particles based on other criteria such as type or nature of the particle (e.g., dead cells, polymer based, having too low or high transparency).

At 758, the image processing module 124 then counts the number of particles in the droplet record that satisfy one or more criteria for the characteristic of interest. For example, particles may be counted that have a size between the upper and lower thresholds. Additionally or alternatively, the image processing module 124 may maintain a separate count of the number of particles for each bin (or for all bins) corresponding to a particle size of interest.

The operations of FIG. 7B are repeated for multiple 3-D images to maintain a count of the number of particles of interest in a corresponding droplet. For example, the counting operation of FIG. 7B may be repeated multiple times with respect to a single droplet, such as before and/or after the droplet undergoes various operations (e.g., assay protocols, etc.).

Optionally, the process of FIG. 7B may further include recirculation operations at 760-762 (e.g., to avoid overlap). At 760, the controller 120 directs the fluidics system to move a current droplet from a first location to a second location. For example, the system may include an image capture device (or multiple image capture devices) that are configured to collect raw 2D images from multiple locations within a fluidics cartridge. In the present example, a droplet may be initially positioned at a first location in the fluidics cartridge where a first raw 2D image is acquired. The droplet is then moved (at 760) from the first location within the fluidics cartridge. The movement at 760 may be to move the droplet from a first location to another location in the fluidics cartridge. Alternatively, the movement at 760 may be to move the droplet away from the first location and the return the droplet to the first location.

At 762, the operations of FIG. 7A are repeated and a second raw 2D image is acquired after the droplet is moved. The second raw 2D image is reconstructed and the reconstructed 3-D image is analyzed to count the number of particles of interest in the droplet (at 764).

For example, the process may utilize a single common image capture device and image capture location. For example, at 760, the controller 120 may direct the fluidics system to move the droplet away from a cartridge illumination zone and then return the droplet to the original cartridge illumination zone. In certain instances, it may be desirable to move a droplet and recount the particles therein in order to improve count accuracy. For example, moving the droplet may avoid counting errors such as when two or more particles overlap (e.g., in the Z-direction). When particles/cells overlap, a diffraction pattern may result that appears as one large object. By moving the droplet and recounting, the process may cause overlapping particles to spatially separate and create separate diffraction patterns.

Optionally, the operations at 760-764 may be repeated more than twice in connection with recirculating a single droplet (e.g., to avoid overlap). Optionally, the operations at 760-764 may be repeated between various operations in an assay protocol.

FIG. 7C illustrates a flow diagram of a method for analyzing reconstructed 3-D images to track cell status in accordance with embodiments herein. The operations of FIG. 7C are performed during the analyzing operation 745 of FIG. 7A. At 772, the image processing module 124 identifies each cell in a current 3-D image 130 and may assign a unique identifier to each cell (e.g., cell ID1, cell ID2, etc.). The image processing module 124 also identifies a criteria of interest (e.g., alive, dead, transparent, size, shape, diameter) associated with each cell. The image processing module 124 may form a droplet record based on the identified cells and criteria of interest.

At 774, the image processing module 124 analyzes the cells to classify the cells based on the criteria of interest. For example, when the criteria of interest relates to cell life or cell health, the cells may be classified as dead, alive, or an intermediate state there between (e.g., semi-healthy, damaged, healthy). When the criteria of interest relates to size, transparency, type and the like, the classification may be based on size thresholds, transparency thresholds, etc. The cell classification is saved with the cell identifier in the droplet record.

At 776, the image processing module 124 analyzes the cell classifications in the droplet record and discards or otherwise removes certain cells from further consideration that do not satisfy the criteria of interest. For example, the image processing module 124 may remove, from the droplet record, cells that have been classified as dead or classified to exhibit a certain percentage likelihood that the cell is dead or unduly unhealthy. As a further example, the image processing module 124 may remove, from the droplet record, cells that have a size or transparency that is greater than a predetermined upper threshold. Additionally or alternatively, the image processing module 124 may remove, from the droplet record, particles based on other criteria such as type or nature of the particle (e.g., polymer based).

Optionally, the image processing module 124 may count the number of cells in the droplet record that satisfy the classification criteria. For example, cells may be counted that are at least 50% alive or have at least a 50% likelihood that the cells are alive.

The operations of FIG. 7C are repeated for multiple 3-D images to maintain a count of the number of cells of interest in a corresponding droplet. For example, the counting operation of FIG. 7C may be repeated multiple times with respect to a single droplet, such as before and after the droplet undergoes various operations (e.g., assay protocols, etc.). The cell IDs in the droplet record may be used to track a progression of a status of the cell (e.g., a progression from alive to dead).

Optionally, the process of FIG. 7C may further include recirculation operations at 780-782 (as explained above in connection with FIG. 7B). At 780, the controller 120 directs the fluidics system to move a current droplet. In the present example, a droplet may be initially positioned at a first location in the fluidics cartridge where a first raw 2D image is acquired. The droplet is then moved (at 780) from the first location within the fluidics cartridge. The movement at 780 may be to move the droplet from a first location to another location in the fluidics cartridge. Alternatively, the movement at 780 may be to move the droplet away from the first location and the return the droplet to the first location.

At 782, the operations of FIG. 7A are repeated and a second raw 2D image is acquired after the droplet is moved. The second raw 2D image is reconstructed and the reconstructed 3-D image is analyzed to classify the status of the cells.

As explained in connection with FIG. 7B, recirculation may be used to avoid overlapping cells in order to improve status accuracy. For example, moving the droplet may avoid classification errors such as when two or more cells overlap (e.g., in the Z-direction). When cells overlap, a diffraction pattern may result that appears as one large object. Also, when cells overlap, one cell may be dead while the other cell is alive. The overlap may cause one or both of the cells to exhibit a diffraction pattern that does not accurately reflect the alive/dead status of the cells. By moving the droplet and reclassifying, the process may cause overlapping cells to spatially separate and create separate diffraction patterns.

Optionally, the operations at 780-784 may be repeated more than twice in connection with recirculating a single droplet (e.g., to avoid overlap). Optionally, the operations at 780-784 may be repeated between various operations in an assay protocol.

Figure 8:
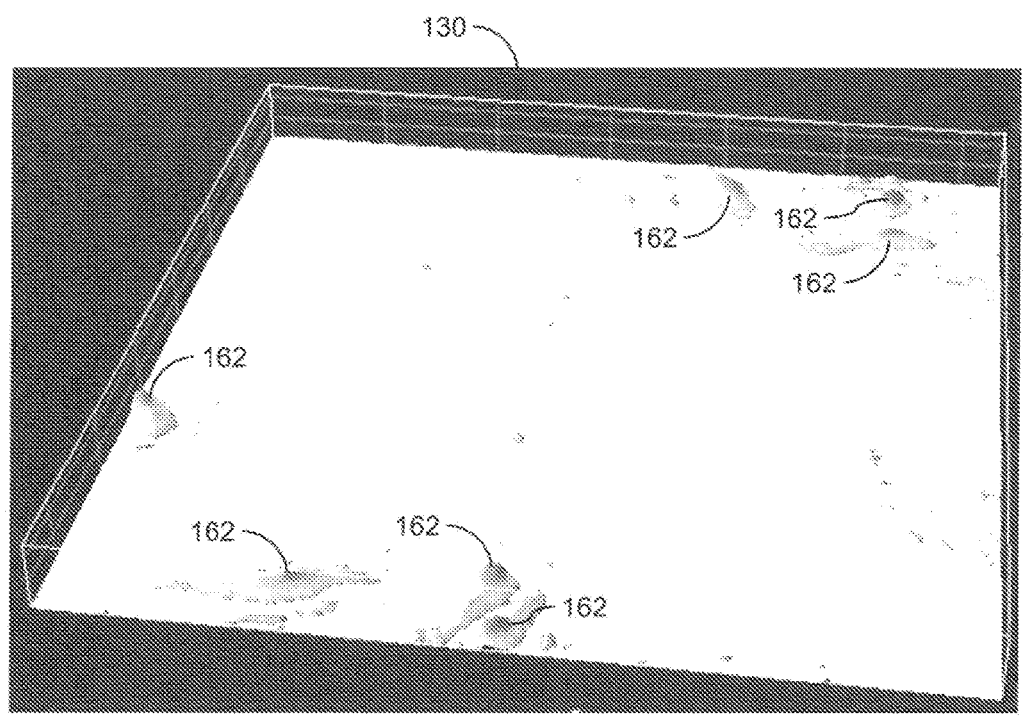
FIG. 8 and FIG. 9 illustrates examples of 3-D images that are generated using a holographic reconstruction process from images captured using the diffraction-based lens-free optical detector in accordance with embodiments herein.
Figure 9:
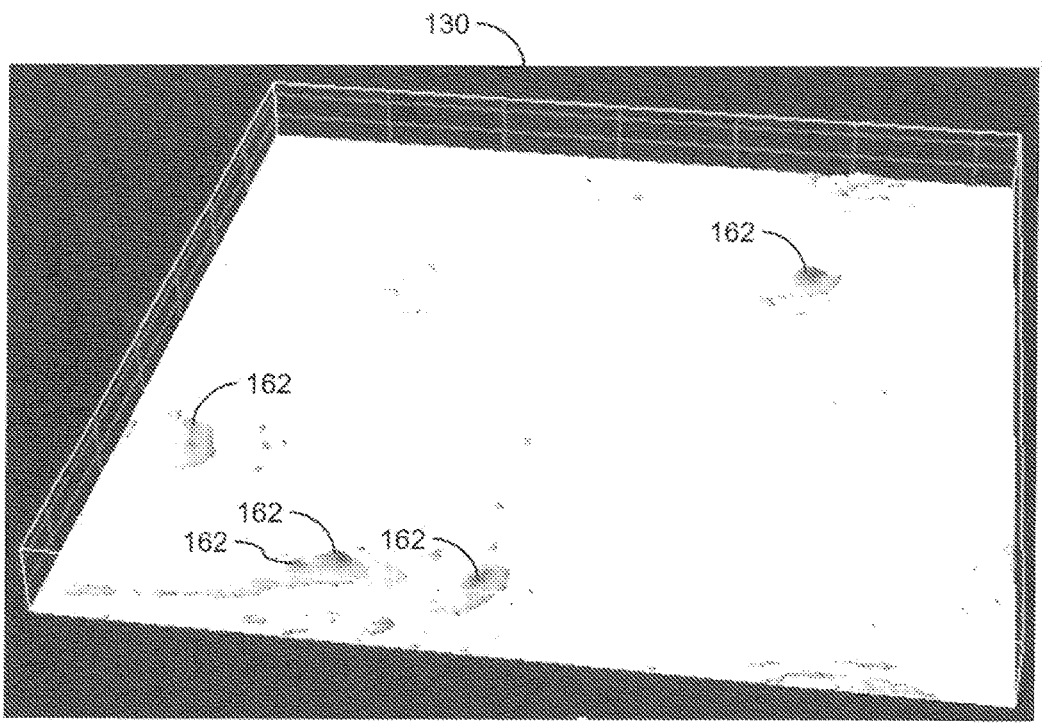

FIG. 8 and FIG. 9 illustrates examples of two reconstructed 3-D images 130 (also referred to as image frames) that are generated by image reconstruction module 122, which uses a holographic reconstruction process of raw images 128 captured using image capture device 114 of diffraction-based lens-free optical detector 110 of microfluidics system 100. The two reconstructed 3-D images 130 are examples of images generated using method steps 740 and 745 of method 700 of FIG. 7A. The two reconstructed 3-D images 130 shown in FIG. 8 and FIG. 9 are time-lapsed images, which show the movement of certain particles 162 over time between first and second image frames.

Figure 10A:
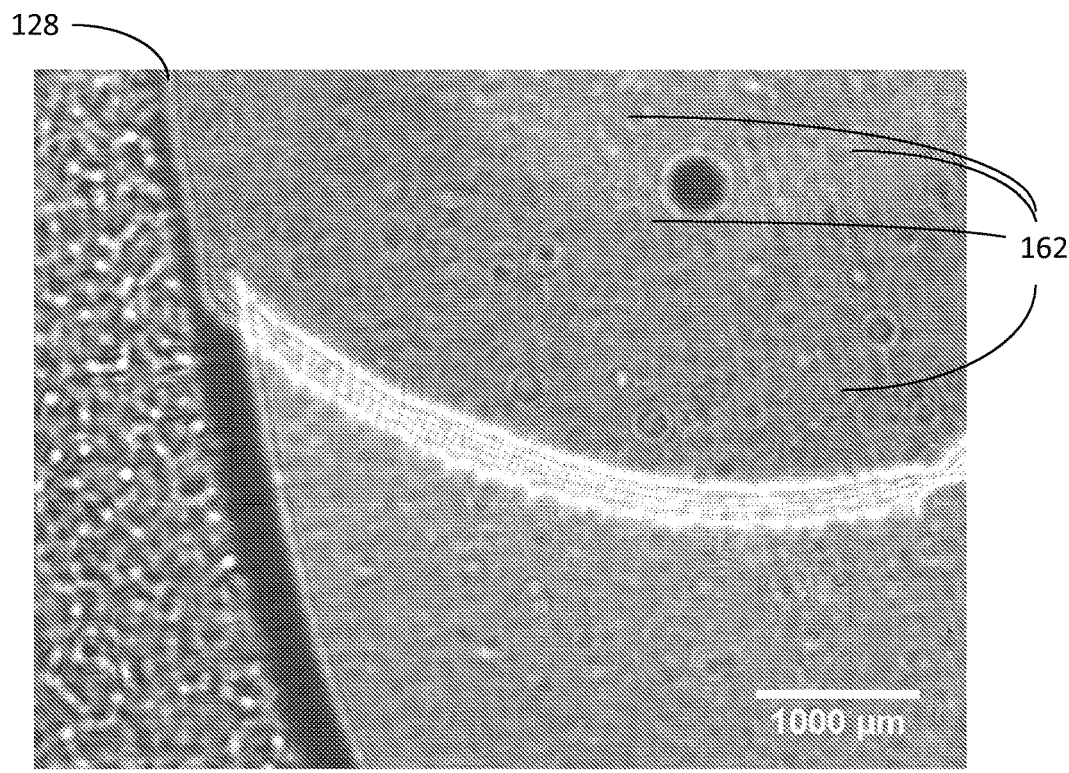
FIG. 10A and FIG. 10B illustrates an example of a raw image and its corresponding post-processed image, respectively, in accordance with embodiments herein.
Figure 10B:
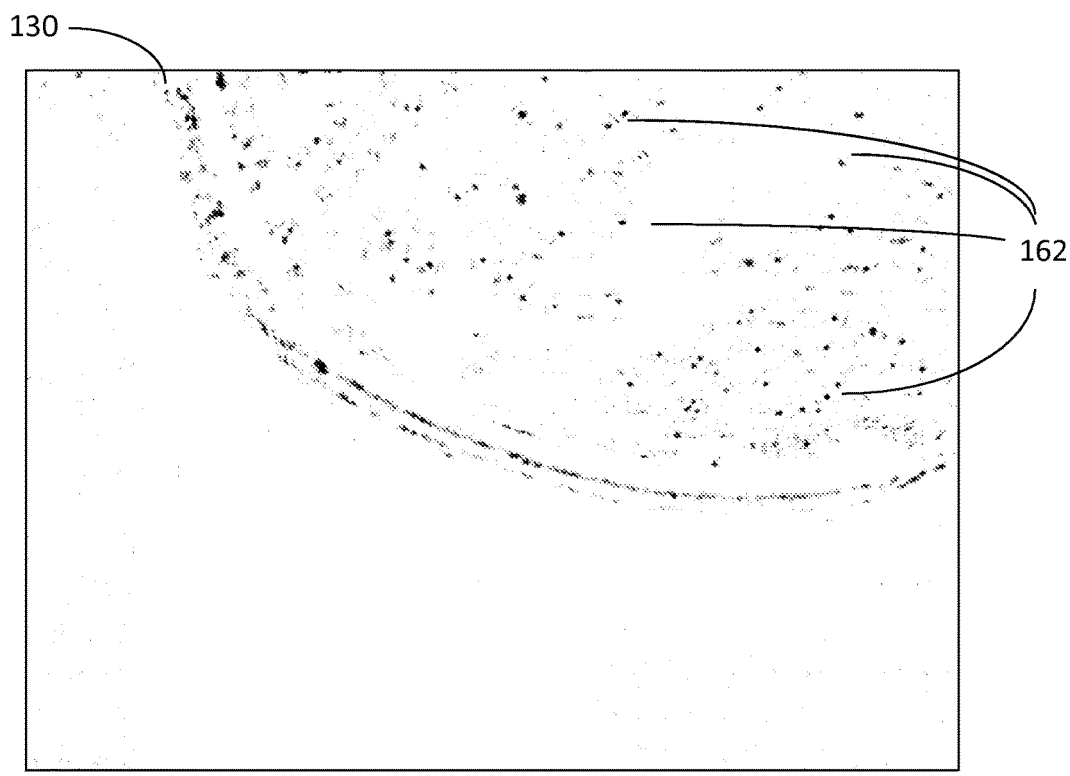
Figure 11A:
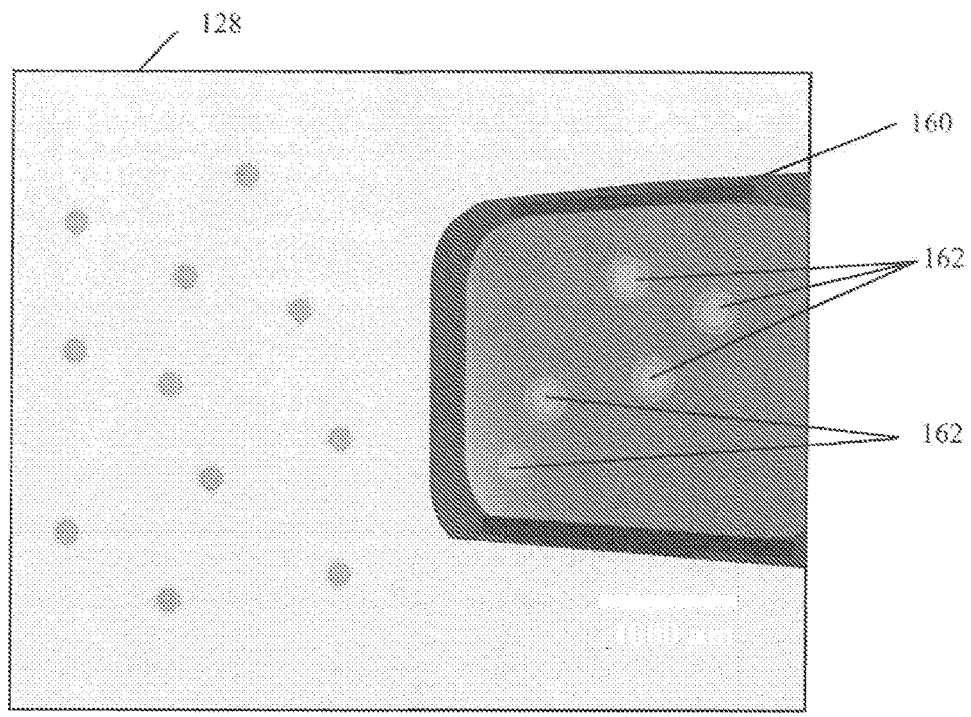
FIG. 11A and FIG. 11B illustrates another example of a raw image and its corresponding post-processed image, respectively, in accordance with embodiments herein.
Figure 11B:
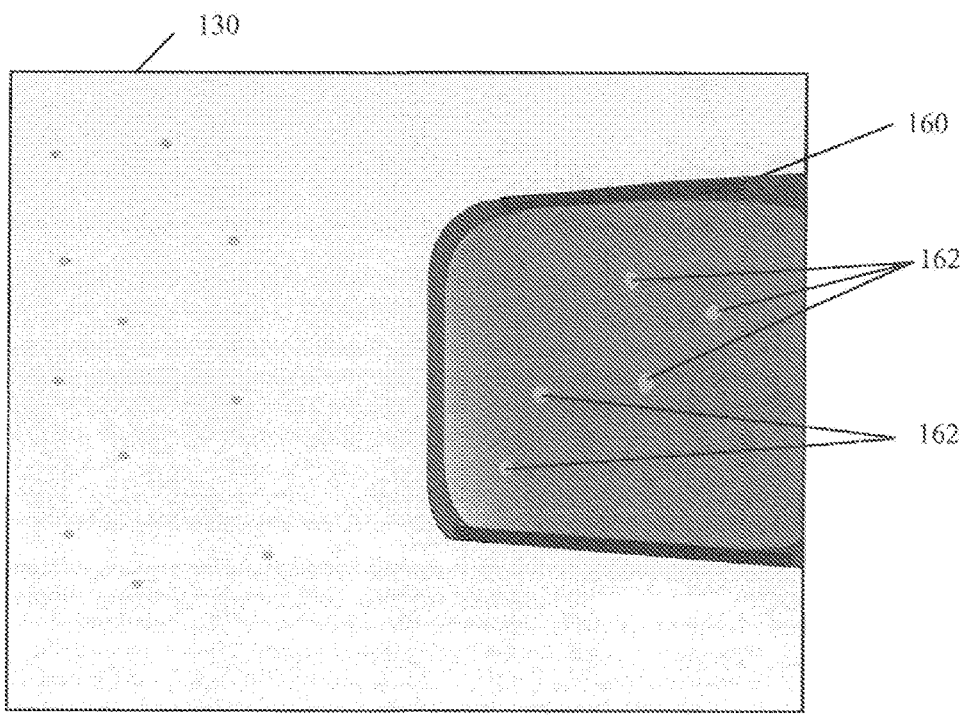

FIG. 10A shows an example of a raw image 128 captured using image capture device 114 of diffraction-based lens-free optical detector 110, which is an example of a raw image 128 captured at method step 725 of method 700 of FIG. 7A. In this example, one of the particles 162 shown in raw image 128 is a 15-μm magnetically responsive bead. FIG. 10B shows an example of the reconstructed 3-D image 130 generated from the raw image 128 shown in FIG. 10A using a holographic reconstruction process of microfluidics system 100 of FIG. 1. Namely, FIG. 10B shows an example of the reconstructed 3-D image 130 generated from the raw image 128 shown in FIG. 10A using method steps 740 and 745 of method 700 of FIG. 7A. Again, in this example, one of the particles 162 shown in reconstructed 3-D image 130 is the 15-μm magnetically responsive bead. Throughout, the elements 162 are referred to as particles, although it is recognized that the elements 162 constitute representations (color or gray scale) of one or more characteristics of interest from a particle or cell. For example, the characteristic of interest may include one or more of basic location, size, general shape or other structures as determined from the diffraction pattern associated therewith (component or composite). It is recognized that the representations designated at 162 may not illustrate an exact location, size or shape of a particle or cell. Instead, the representations at 162 may illustrate approximations of the location, size, shape or other characteristic(s) of interest from the particle or cell. FIG. 11A shows another example of a raw image 128 captured using image capture device 114 of diffraction-based lens-free optical detector 110, which is an example of a raw image 128 captured at method step 725 of method 700 of FIG. 7A. In this example, the particles 162 in the sample droplet 160 shown in raw image 128 are 15-μm magnetically responsive beads. FIG. 11B shows an example of the reconstructed 3-D image 130 generated from the raw image 128 shown in FIG. 11A using a holographic reconstruction process of microfluidics system 100 of FIG. 1. Namely, FIG. 11B shows an example of the reconstructed 3-D image 130 generated from the raw image 128 shown in FIG. 10A using method steps 740 and 745 of method 700 of FIG. 7A. Again, in this example, the particles 162 shown in reconstructed 3-D image 130 are the 15-μm magnetically responsive beads.

Figure 12A:
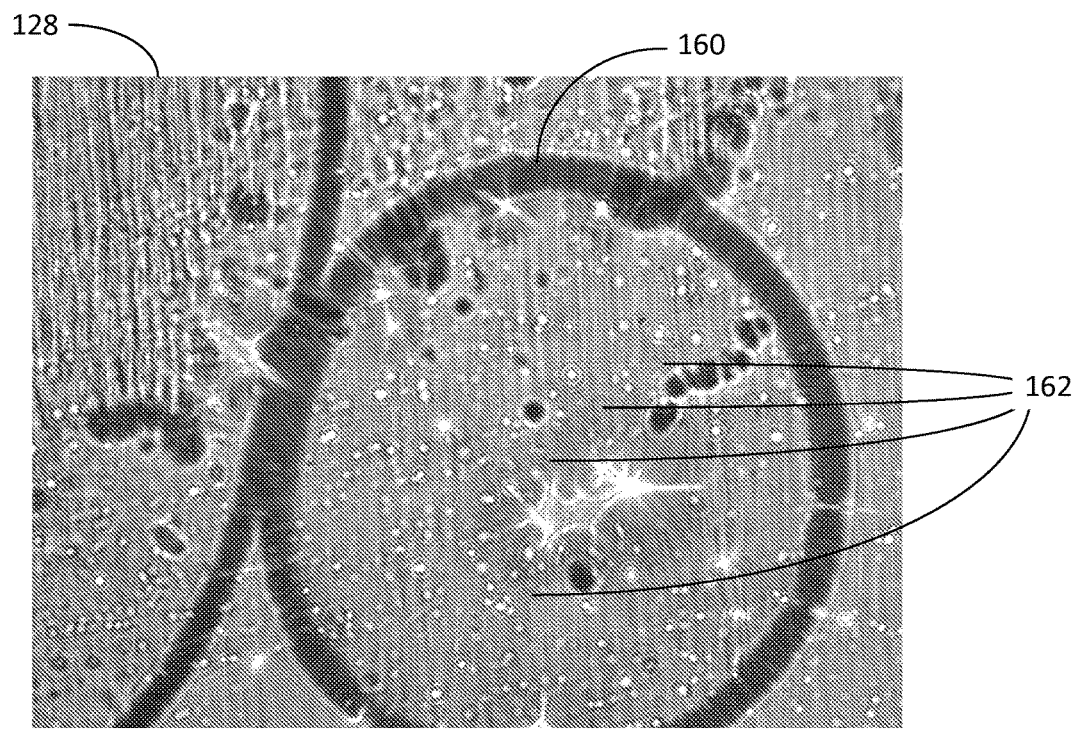
FIG. 12A and FIG. 12B illustrates yet another example of a raw image and its corresponding post-processed image, respectively, in accordance with embodiments herein.
Figure 12B:
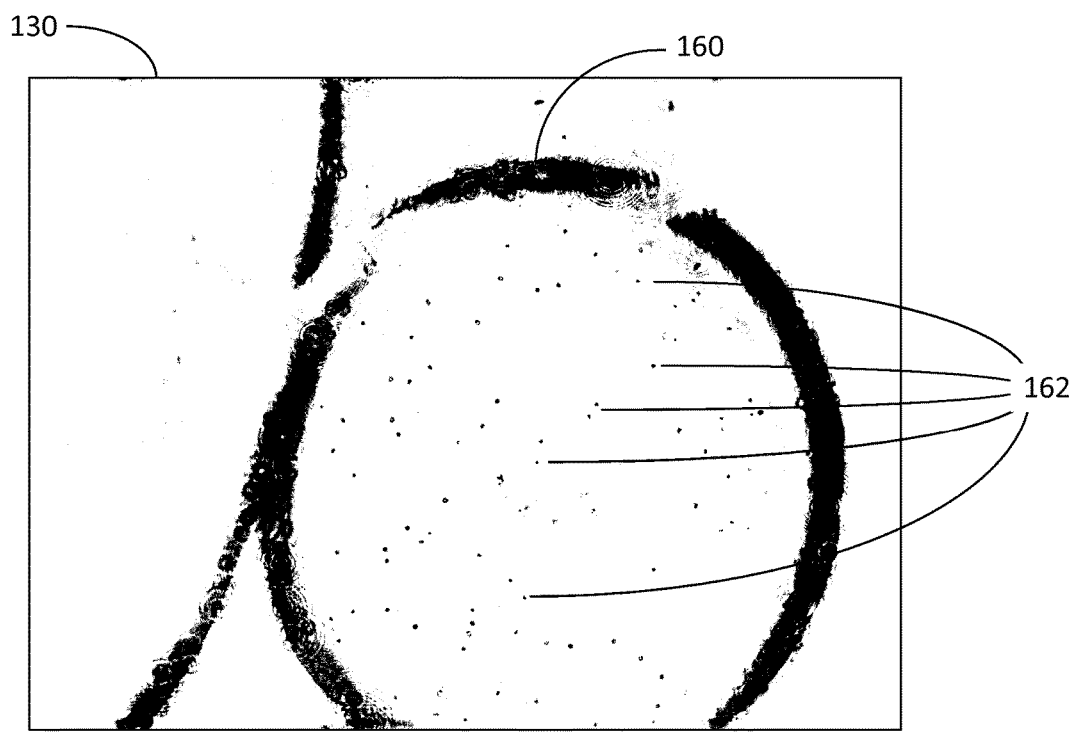

FIG. 12A shows another example of a raw image 128 captured using image capture device 114 of diffraction-based lens-free optical detector 110, which is an example of a raw image 128 captured at method step 725 of method 700 of FIG. 7A. In this example, the sample droplet 160 has a diameter of about 4 mm and a volume of about 1.6 μl. Further, the particles 162 in the sample droplet 160 shown in raw image 128 are 10-μm to 20-μm cells. FIG. 12B shows an example of the reconstructed 3-D image 130 generated from the raw image 128 shown in FIG. 12A using a holographic reconstruction process of microfluidics system 100 of FIG. 1. Namely, FIG. 12B shows an example of the reconstructed 3-D image 130 generated from the raw image 128 shown in FIG. 10A using method steps 740 and 745 of method 700 of FIG. 7A. Again, in this example, the particles 162 shown in reconstructed 3-D image 130 are the 10-μm to 20-μm cells.

Figure 13A:
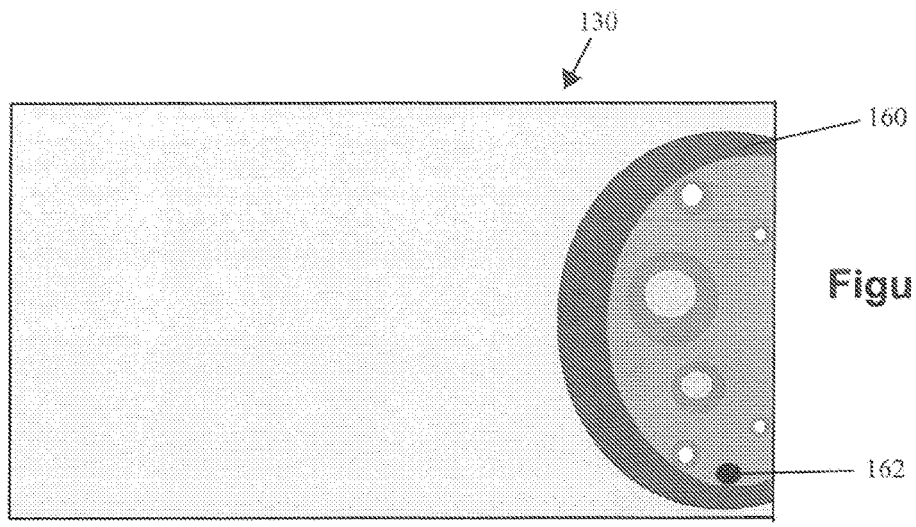
FIG. 13A, FIG. 13B, and FIG. 13C illustrates a time-lapsed sequence of post-processed images, which shows cells moving with the droplet in accordance with embodiments herein.
Figure 13B:
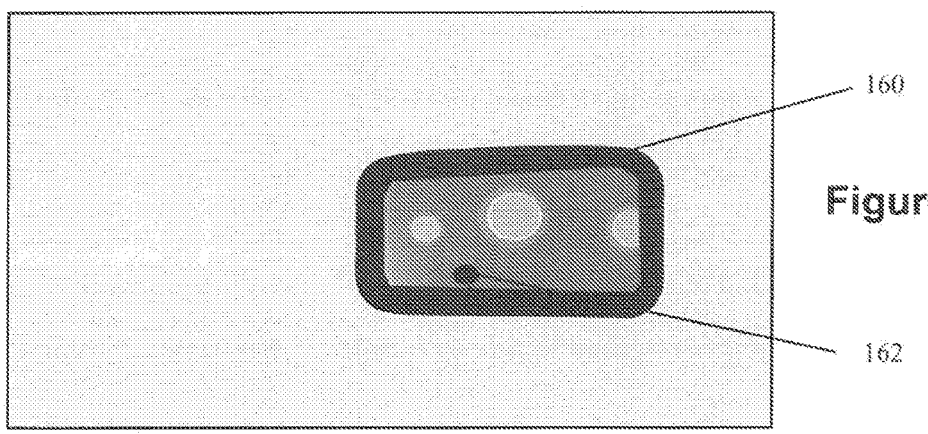
Figure 13C:
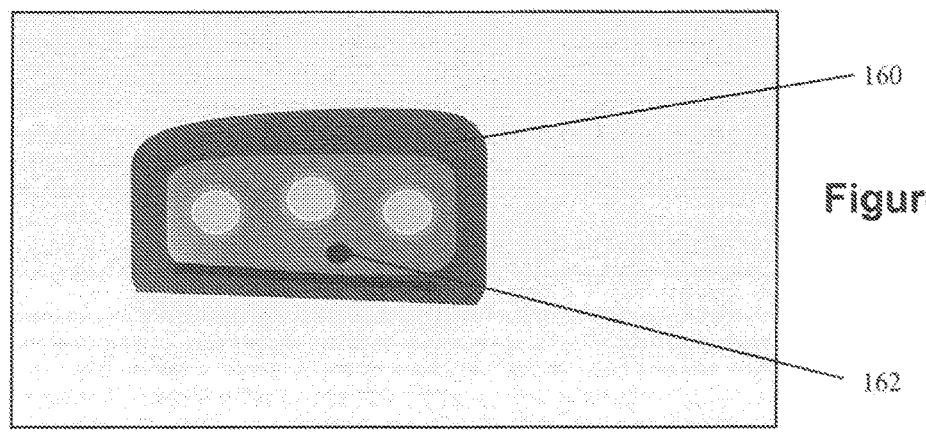

FIG. 13A, FIG. 13B, and FIG. 13C show an example of a time-lapsed sequence of reconstructed 3-D images 130, which shows particles 162 (e.g., cells) moving along with the sample droplet 160 during droplet operations.

Referring now to FIG. 1 through FIG. 13C, some of the features/advantages of microfluidics system 100 and method 700 can be summarized as follows: (1) using diffraction-based lens-free optical detector 110, a large area can be imaged using a lens-free imaging configuration as compared with conventional microscopy; (2) image reconstruction module 122 can process a 2-D image of a diffraction pattern from image capture device 114 and then generate a high quality 3-D image of particles in the sample liquid, which obviates the need for z-scanning that is required using conventional microscopy; (3) because z-scanning is not required, fast time-lapse acquisition is possible; and (4) microfluidics system 100 and method 700 can be highly useful with regard to single cell technology, wherein determining the genetic information of a single cell is very important.

Further, the presently disclosed microfluidics system 100 and method 700 can be used with various kinds of applications and droplet operations. For example, microfluidics system 100 and method 700 can be used during dispensing operations until a certain specified number of cells in a droplet is achieved, such as a single cell in a droplet. Then, using the droplet with the specified number of cells in downstream processes, such as an assay. In another example, the presently disclosed microfluidics system 100 and method 700 can be used to take a droplet containing two cells and then split the droplet into two droplets, each containing one cell.

Figure 14:
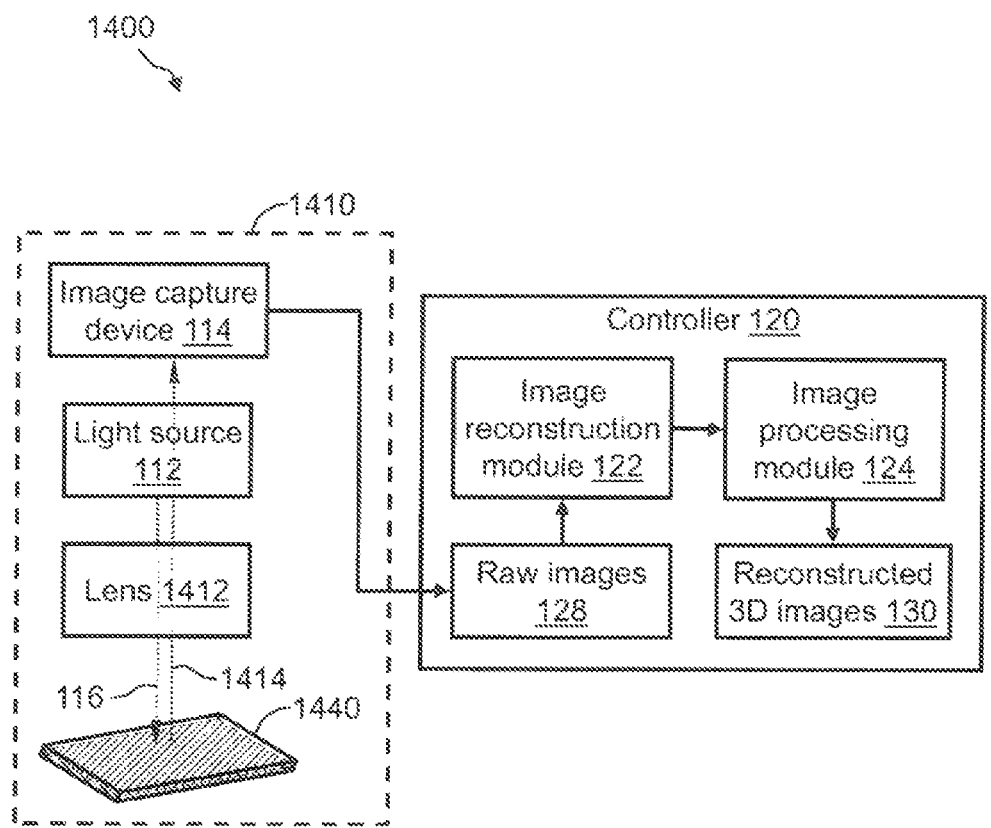
FIG. 14 illustrates a block diagram of an example of a microfluidics system in accordance with embodiments herein.

FIG. 14 illustrates a block diagram of an example of a microfluidics system 1400 for identifying and/or tracking particles in a droplet. Microfluidics system 1400 is substantially the same as microfluidics system 100 of FIG. 1 except that diffraction-based lens-free optical detector 110 is replaced with a reflection interference-based optical detector 1410. Further, whereas diffraction-based lens-free optical detector 110 of microfluidics system 100 operates in transmission mode with a substantially transparent fluidics cartridge, reflection interference-based optical detector 1410 of microfluidics system 1400 operates in reflection mode with a substantially non-transparent fluidics cartridge.

Microfluidics system 1400 includes controller 120 that further includes image reconstruction module 122 and image processing modules 124, as described with reference to microfluidics system 100 of FIG. 1.

Reflection interference-based optical detector 1410 includes light source 112 and image capture device 114, as described with reference to microfluidics system 100 of FIG. 1. Reflection interference-based optical detector 1410 further includes a lens 1412. Lens 1412 can be a low magnification lens. Lens 1412 can range, for example, from about 2× magnification to about 10× magnification. In one example, lens 1412 is a 4× magnification lens. Lens 1412 has a FOV that is large enough to capture an image of droplet 160 in its entirety. In one example, lens 1412 has a FOV of about 30 mm².

Reflection interference-based optical detector 1410 is used in combination with a substantially non-transparent fluidics cartridge, such as a non-transparent fluidics cartridge 1440. More details of non-transparent fluidics cartridge 1440 are shown and described hereinbelow with reference to FIG. 15A and FIG. 15B. In reflection interference-based optical detector 1410, lens 1412 is directed toward non-transparent fluidics cartridge 1440 and light source 112 is used to illuminate non-transparent fluidics cartridge 1440. Light 116 emitted from light source 112 strikes the sample liquid and certain reflective surfaces in non-transparent fluidics cartridge 1440 and the combination of both diffracted light and reflected light is returned to image capture device 114. For example, light 1414 is returned to image capture device 114, wherein light 1414 is the combination of both diffracted light and reflected light. More details of reflection interference-based optical detector 1410 in relation to non-transparent fluidics cartridge 1440 are shown and described hereinbelow with reference to FIG. 16.

Figure 15A:
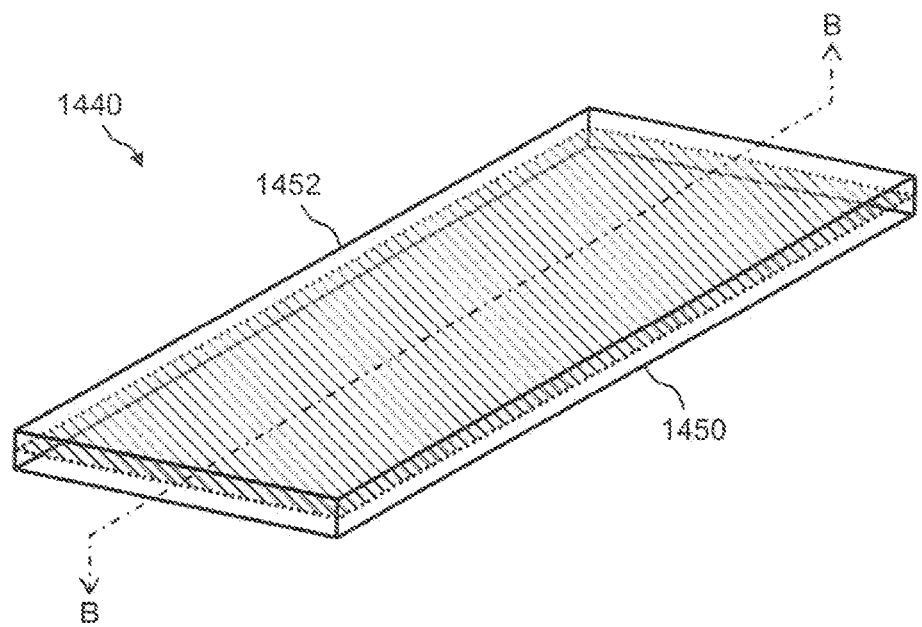
FIG. 15A illustrates a perspective view of an example of a substantially non-transparent fluidics cartridge in accordance with embodiments herein.
Figure 15B:
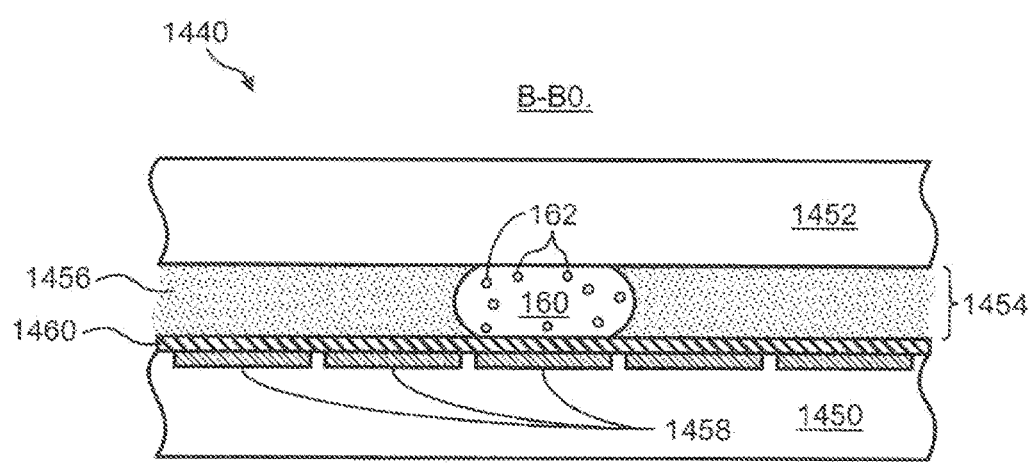
FIG. 15B illustrates a cross-sectional view of a portion of the substantially non-transparent fluidics cartridge shown in FIG. 15A taken along line B-B.

FIG. 15A illustrates a perspective view of an example of the substantially non-transparent fluidics cartridge 1440. FIG. 15B illustrates a cross-sectional view of a portion of non-transparent fluidics cartridge 1440 taken along line B-B of FIG. 15A. Non-transparent fluidics cartridge 1440 includes a bottom substrate 1450 and a top substrate 1452 that are separated by a droplet operations gap 1454. Droplet operations gap 1454 contains filler fluid 1456. The filler fluid 1456 is, for example, low-viscosity oil, such as silicone oil or hexadecane filler fluid. Bottom substrate 1450 may include an arrangement of droplet operations electrodes 1458 (e.g., electrowetting electrodes). Top substrate 1452 may include a ground reference plane or electrode (not shown). Droplet operations are conducted atop droplet operations electrodes 1458 on a droplet operations surface. For example, FIG. 15B shows droplet 160 in droplet operations gap 1454 and atop one of the droplet operations electrodes 1458. With respect to non-transparent fluidics cartridge 1440, controller 120 or any other controller (not shown) may be used to control droplet manipulation by activating/deactivating droplet operations electrodes 1458.

Top substrate 1452 and the ground reference plane or electrode (not shown) are formed of materials that are substantially transparent to light, such as to light 116 emitted from light source 112. In one example, top substrate 1452 is formed of glass or plastic, while the ground reference plane or electrode (not shown) is formed of ITO.

In one example, bottom substrate 1450 is a PCB and droplet operations electrodes 1458 are formed of copper or gold. Bottom substrate 1450 and/or droplet operations electrodes 1458 are not transparent to light, thereby forming substantially non-transparent fluidics cartridge 1440. Namely, light can pass through top substrate 1452 and the ground reference plane or electrode (not shown), but not through bottom substrate 1450 and/or droplet operations electrodes 1458.

Further, a reflective layer 1460 is provided atop bottom substrate 1450 and droplet operations electrodes 1458. Reflective layer 1460 can be a single layer of material or can include multiple layers of materials. Reflective layer 1460 can have varying degrees of reflectivity. In one example, reflective layer 1460 is a single layer of black KAPTON®. KAPTON® is a polyimide film, available from DuPont, Wilmington, Del. In another example, reflective layer 1460 is a single layer of yellow KAPTON®. In yet another example, reflective layer 1460 includes a layer of black KAPTON® and a layer of mirror material, such as a 50-nm thick layer of platinum. For example, a layer of black KAPTON® atop bottom substrate 1450, then the platinum layer atop the KAPTON® layer. In still another example, reflective layer 1460 includes a layer of yellow KAPTON® and a layer of mirror material, such as the 50-nm thick layer of platinum.

Figure 16:
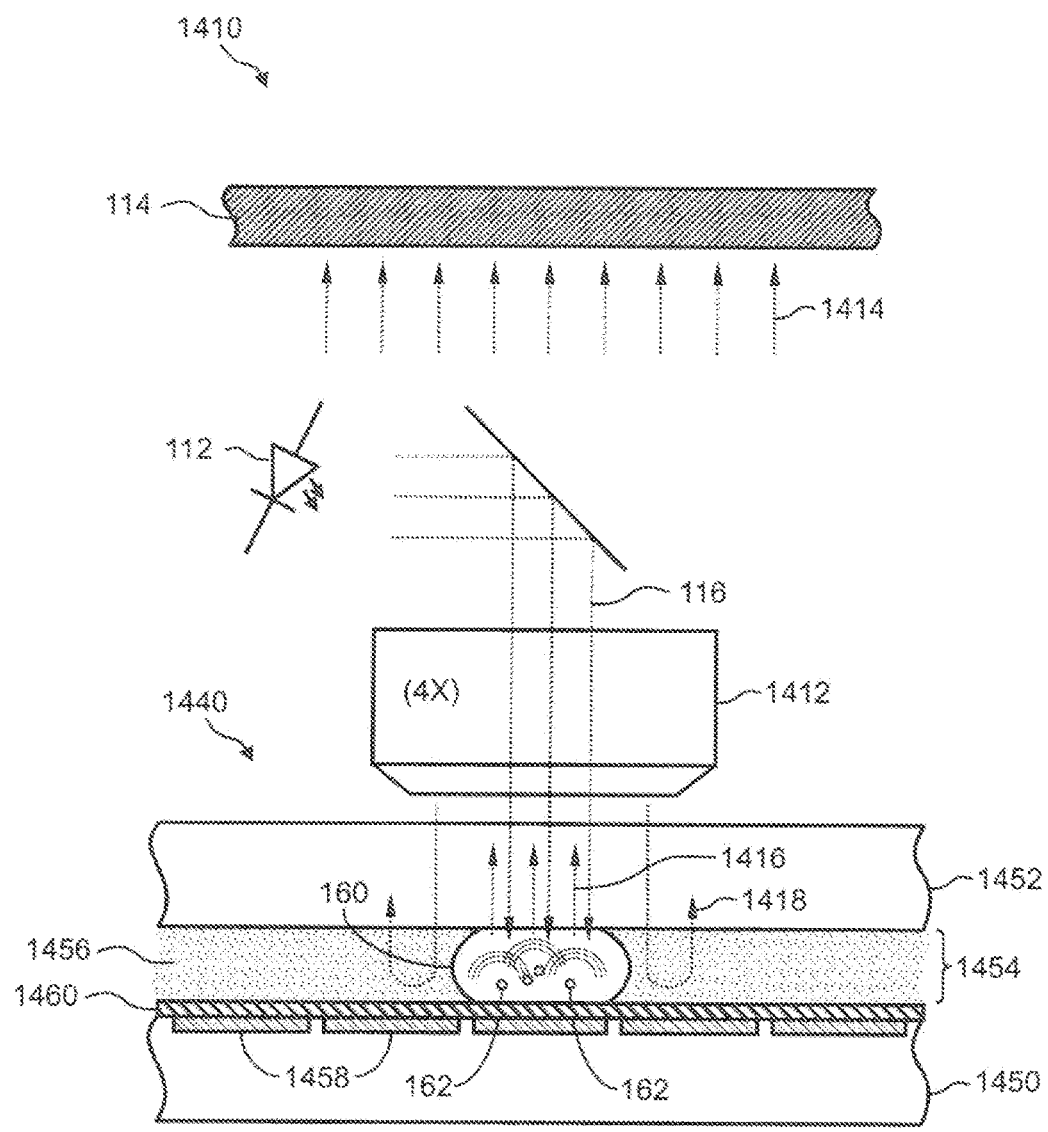
FIG. 16 illustrates the reflection interference-based optical detector of the microfluidics system of FIG. 14 when in use with the non-transparent fluidics cartridge of FIG. 15A and FIG. 15B in accordance with embodiments herein.

FIG. 16 shows more details (not drawn to scale) of an example of reflection interference-based optical detector 1410 of microfluidics system 1400 of FIG. 14 when in use with non-transparent fluidics cartridge 1440 of FIG. 15A and FIG. 15B. In this example, light source 112 is a green LED, lens 1412 is a 4× magnification lens, and reflective layer 1460 includes a yellow KAPTON® layer and a 50-nm thick platinum layer.

Reflection interference-based optical detector 1410 operates in refection mode, meaning that light 116 emitted from light source 112 is fully or in part reflected off of, for example, reflective layer 1460 of non-transparent fluidics cartridge 1440 and returned to image capture device 114. More particularly, a combination of both reflected light and diffracted light is returned to image capture device 114. For example, FIG. 16 shows diffracted light 1416, which is diffraction light off of particles 162 in sample droplet 160. FIG. 16 also shows reflected light 1418, which is light that is reflected off of reflective layer 1460 and returned to image capture device 114. Accordingly, light 1414 that reaches image capture device 114 is a combination of both diffracted light 1416 and reflected light 1418.

By providing provision in non-transparent fluidics cartridge 1440 to generate both diffracted light 1416 and reflected light 1418, the optical signal received at image capture device 114 is stronger than would be generated using diffracted light 1416 alone. Namely, the interference between diffracted light 1416 and reflected light 1418 creates a stronger signal back to image capture device 114 as compared with the signal from diffracted light 1416 alone. In so doing, image capture device 114 captures an image of the diffraction pattern of droplet 160 and particles 162 (and any features of non-transparent fluidics cartridge 1440).

A method of using microfluidics system 1400 of FIG. 14 to identify and/or track particles in a droplet, wherein the particle can be a cell, is substantially the same as method 700 of FIG. 7A except that in method step 710, microfluidics system 1400 of FIG. 14 is provided instead of microfluidics system 100 of FIG. 1. Accordingly, in method step 725, image capture device 114 of reflection interference-based optical detector 1410 is used instead of image capture device 114 of diffraction-based lens-free optical detector 110. Further, in method step 730, reflection interference-based optical detector 1410 provides the raw image 128 to image reconstruction module 122 at controller 120 instead of diffraction-based lens-free optical detector 110.

Figure 17:
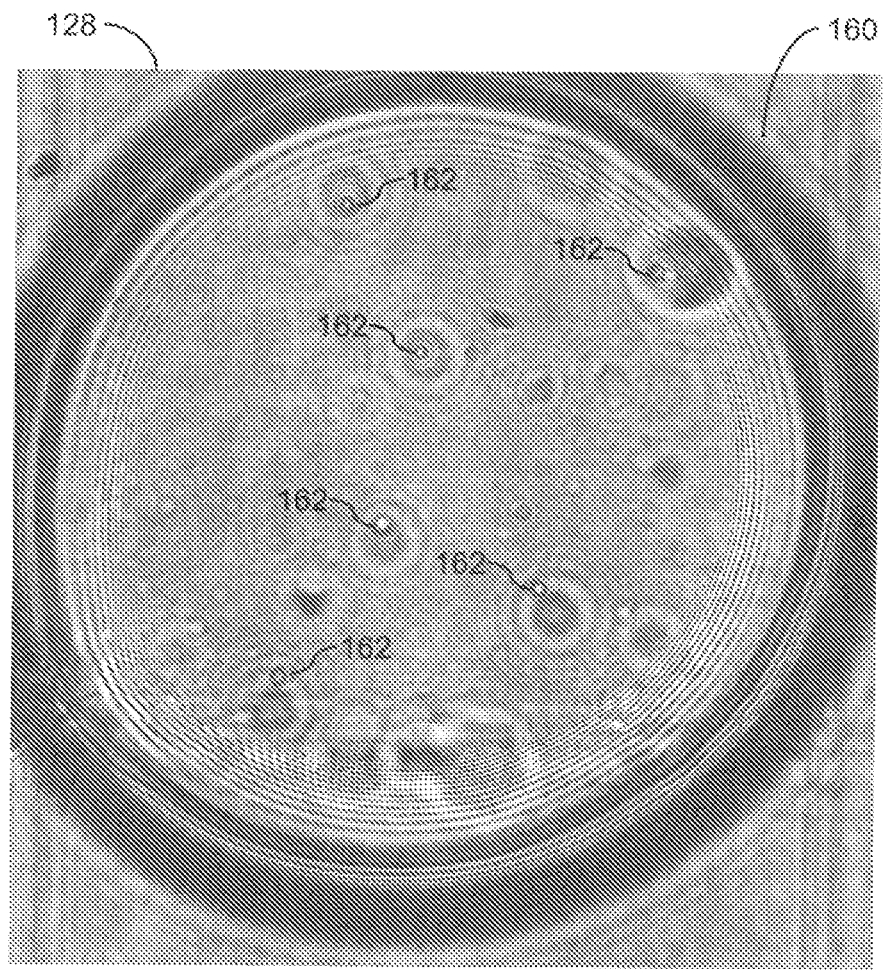
FIG. 17 and FIG. 18 illustrates an example of a raw image and its corresponding post-processed image, respectively, of the microfluidics system of FIG. 14 in accordance with embodiments herein.
Figure 18:
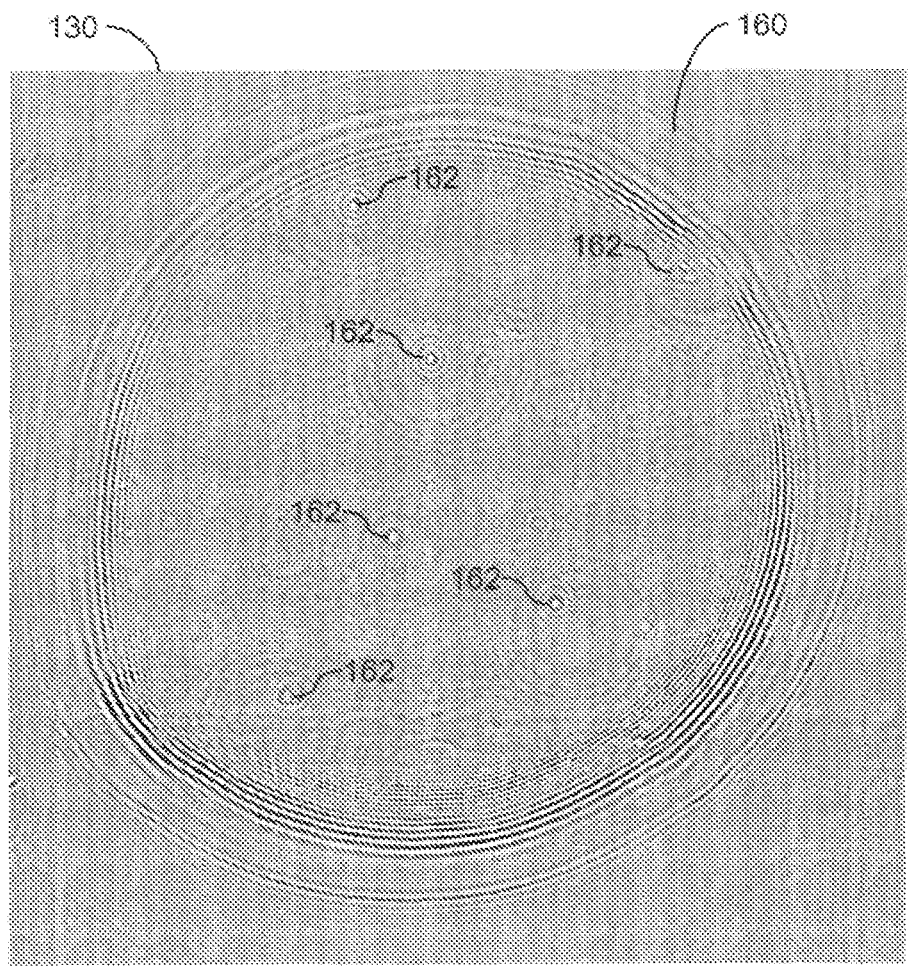

FIG. 17 shows an example of a raw image 128 captured using image capture device 114 of reflection interference-based optical detector 1410, which is an example of a raw image 128 captured at method step 725 of method 700 of FIG. 7A. In this example, the particles 162 in the sample droplet 160 shown in raw image 128 include a plurality of 10-µm to 20-µm cells. FIG. 18 shows an example of the reconstructed 3-D image 130 generated from the raw image 128 shown in FIG. 17 using image reconstruction module 122 and/or image processing modules 124 of microfluidics system 1400 of FIG. 14. Namely, FIG. 18 shows an example of the reconstructed 3-D image 130 generated from the raw image 128 shown in FIG. 17 using method steps 740 and 745 of method 700 of FIG. 7A. Again, in this example, the particles 162 shown in reconstructed 3-D image 130 include the 10-µm to 20-µm cells.

Referring now to FIG. 14 through FIG. 18, some of the features/advantages of microfluidics system 1400 can be summarized as follows: (1) using reflection interference-based optical detector 1410, a large area can be imaged using the low magnification lens 1412 as compared with conventional microscopy; (2) image reconstruction module 122 can process a 2-D image of a diffraction pattern from image capture device 114 and then generate a high quality 3-D image of particles in the sample liquid, which obviates the need for z-scanning that is required using conventional microscopy; (3) because z-scanning is not required, fast time-lapse acquisition is possible; and (4) microfluidics system 1400 can be highly useful with regard to single cell technology, wherein determining the genetic information of a single cell is very important.

Further, the presently disclosed microfluidics system 1400 and method 700 can be used with various kinds of applications and droplet operations. For example, microfluidics system 1400 and method 700 can be used during dispensing operations until a certain specified number of cells in a droplet is achieved, such as a single cell in a droplet. Then, using the droplet with the specified number of cells in downstream processes, such as an assay. In another example, the presently disclosed microfluidics system 1400 and method 700 can be used to take a droplet containing two cells and then split the droplet into two droplets, each containing one cell.

Figure 19:
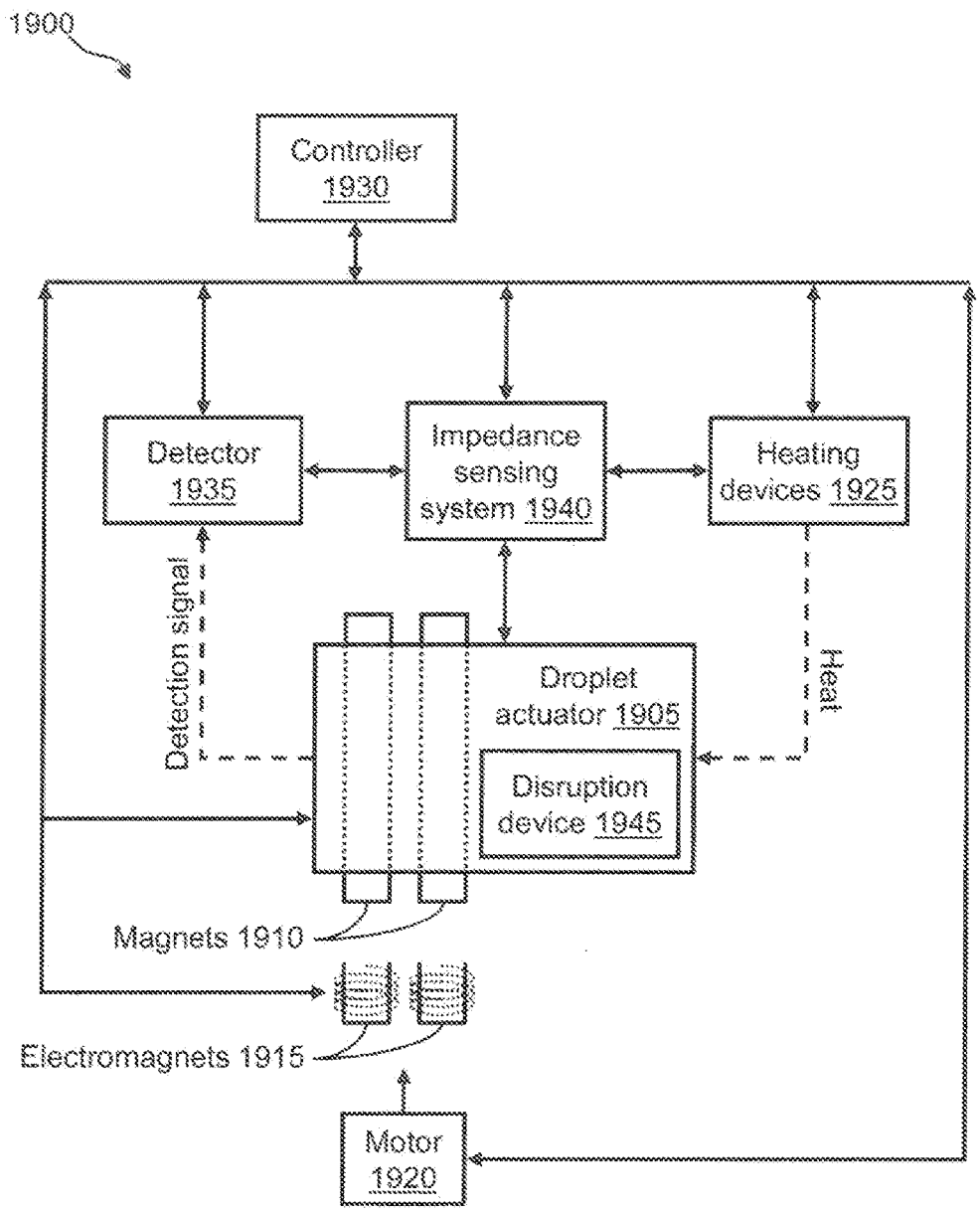
FIG. 19 illustrates a functional block diagram of an example of a microfluidics system that includes a droplet actuator in accordance with embodiments herein.

FIG. 19 illustrates a functional block diagram of an example of a microfluidics system 1900 that includes a fluidics cartridge; namely, a droplet actuator 1905. Digital microfluidic technology conducts droplet operations on discrete droplets in a droplet actuator, such as droplet actuator 1905, by electrical control of their surface tension (electrowetting). The droplets may be sandwiched between two substrates of droplet actuator 1905, a bottom substrate and a top substrate separated by a droplet operations gap. The bottom substrate may include an arrangement of electrically addressable electrodes. The top substrate may include a reference electrode plane made, for example, from conductive ink or indium tin oxide (ITO). The bottom substrate and the top substrate may be coated with a hydrophobic material. Droplet operations are conducted in the droplet operations gap. The space around the droplets (e.g., the gap between bottom and top substrates) may be filled with an immiscible inert fluid, such as silicone oil, to prevent evaporation of the droplets and to facilitate their transport within the device. Other droplet operations may be effected by varying the patterns of voltage activation; examples include merging, splitting, mixing, and dispensing of droplets.

Droplet actuator 1905 may be designed to fit onto an instrument deck (not shown) of microfluidics system 1900. The instrument deck may hold droplet actuator 1905 and house other droplet actuator features, such as, but not limited to, one or more magnets and one or more heating devices. For example, the instrument deck may house one or more magnets 1910, which may be permanent magnets. Optionally, the instrument deck may house one or more electromagnets 1915. Magnets 1910 and/or electromagnets 1915 are positioned in relation to droplet actuator 1905 for immobilization of magnetically responsive beads. Optionally, the positions of magnets 1910 and/or electromagnets 1915 may be controlled by a motor 1920. Additionally, the instrument deck may house one or more heating devices 1925 for controlling the temperature within, for example, certain reaction and/or washing zones of droplet actuator 1905. In one example, heating devices 1925 may be heater bars that are positioned in relation to droplet actuator 1905 for providing thermal control thereof.

A controller 1930 of microfluidics system 1900 is electrically coupled to various hardware components of the apparatus set forth herein, such as droplet actuator 1905, electromagnets 1915, motor 1920, and heating devices 1925, as well as to a detector 1935, an impedance sensing system 1940, and any other input and/or output devices (not shown). Controller 1930 controls the overall operation of microfluidics system 1900. Controller 1930 may, for example, be a general purpose computer, special purpose computer, personal computer, or other programmable data processing apparatus. Controller 1930 serves to provide processing capabilities, such as storing, interpreting, and/or executing software instructions, as well as controlling the overall operation of the system. Controller 1930 may be configured and programmed to control data and/or power aspects of these devices. For example, in one aspect, with respect to droplet actuator 1905, controller 1930 controls droplet manipulation by activating/deactivating electrodes.

In one example, detector 1935 may be an imaging system that is positioned in relation to droplet actuator 1905. In one example, the imaging system may include one or more light-emitting diodes (LEDs) (e.g., an illumination source) and a digital image capture device, such as a charge-coupled device (CCD) camera. Detection can be carried out using an apparatus suited to a particular reagent or label in use. For example, an optical detector such as a fluorescence detector, absorbance detector, luminescence detector or the like can be used to detect appropriate optical labels. Systems designed for array-based detection are particularly useful. For example, optical systems for use with the methods set forth herein may be constructed to include various components and assemblies as described in Banerjee et al., U.S. Pat. No. 8,241,573, entitled "Systems and Devices for Sequence by Synthesis Analysis," issued on Aug. 14, 2012; Feng et al., U.S. Pat. No. 7,329,860, entitled "Confocal Imaging Methods and Apparatus," issued on Feb. 12, 2008; Feng et al., U.S. Pat. No. 8,039,817, entitled "Compensator for Multiple Surface Imaging," issued on Oct. 18, 2011; Feng et al., U.S. Patent Pub. No. 20090272914, entitled "Compensator for Multiple Surface Imaging," published on Nov. 5, 2009; and Reed et al., U.S. Patent Pub. No. 20120270305, entitled "Systems, Methods, and Apparatuses to Image a Sample for Biological or Chemical Analysis," published on Oct. 25, 2012, the entire disclosures of which are incorporated herein by reference. Such detection systems are particularly useful for nucleic acid sequencing embodiments.

Impedance sensing system 1940 may be any circuitry for detecting impedance at a specific electrode of droplet actuator 1905. In one example, impedance sensing system 1940 may be an impedance spectrometer. Impedance sensing system 1940 may be used to monitor the capacitive loading of any electrode, such as any droplet operations electrode, with or without a droplet thereon. For examples of suitable capacitance detection techniques, see Sturmer et al., International Patent Pub. No. WO/2008/101194, entitled "Capacitance Detection in a Droplet Actuator," published on Dec. 30, 1909; and Kale et al., International Patent Pub. No. WO/2002/080822, entitled "System and Method for Dispensing Liquids," published on Feb. 26, 1904, the entire disclosures of which are incorporated herein by reference.

Droplet actuator 1905 may include disruption device 1945. Disruption device 1945 may include any device that promotes disruption (lysis) of materials, such as tissues, cells and spores in a droplet actuator. Disruption device 1945 may, for example, be a sonication mechanism, a heating mechanism, a mechanical shearing mechanism, a bead beating mechanism, physical features incorporated into the droplet actuator 1905, an electric field generating mechanism, armal cycling mechanism, and any combinations thereof. Disruption device 1945 may be controlled by controller 1930.

It will be appreciated that various aspects of the present disclosure may be embodied as a method, system, computer readable medium, and/or computer program product. Aspects of the present disclosure may take the form of hardware embodiments, software embodiments (including firmware, resident software, micro-code, etc.), or embodiments combining software and hardware aspects that may all generally be referred to herein as a "circuit," "module," or "system." Furthermore, the methods of the present disclosure may take the form of a computer program product on a computer-usable storage medium having computer-usable program code embodied in the medium.

Any suitable computer useable medium may be utilized for software aspects of the present disclosure. The computer-usable or computer-readable medium may be, for example but not limited to, an electronic, magnetic, optical, electro-magnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the methods and apparatus set forth herein may be written in an object oriented programming language such as Java, Smalltalk, C++ or the like. However, the program code for carrying out operations of the methods and apparatus set forth herein may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The methods and apparatus set forth herein may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The methods and apparatus set forth herein may be applied to any wireless/wireline communications network, regardless of physical componentry, physical configuration, or communications standard(s).

Certain aspects of present disclosure are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the present disclosure.

The foregoing detailed description of embodiments refers to the accompanying drawings, which illustrate specific embodiments of the present disclosure. Other embodiments having different structures and operations do not depart from the scope of the present disclosure. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the present invention may be changed without departing from the scope of the present invention. Furthermore, the foregoing description is for the purpose of illustration only, and not for the purpose of limitation.

The invention claimed is:

1. A method for performing microfluidics imaging, comprising:
   positioning a fluidics cartridge at a cartridge illumination zone, the fluidics cartridge including top and bottom substrates separated by a droplet operations gap, the droplet operations gap configured to retain a filler fluid including at least one sample droplet containing one or more particles of interest;
   emitting light onto the cartridge illumination zone;
   capturing a raw two-dimensional (2-D) image containing a particle diffraction pattern corresponding to the one or more particles of interest utilizing an image capture device that is held in a predetermined relation relative to the light source and cartridge illumination zone; and
   utilizing one or more processors for analysis of reconstructed 3-D images to count one or more particles of interest in the sample droplet, the analysis comprising:
   (a) identifying, using the one or more processors, particles in a 3-D image and identifying criteria of interest associated with the particles;
   (b) forming, using the one or more processors, a droplet record based on the particles and criteria of interest;
   (c) grouping, using the one or more processors, the particles in the droplet record into one or more bins based on the criteria of interest;
   (d) analyzing, using the one or more processors, the one or more bins in the droplet record and removing particles from the one or more bins that do not satisfy the criteria of interest; and
   (e) counting, using the one or more processors, the number of particles in the one or more bins.

2. The method of claim 1, further comprising operating the light source and image capture device in a transmission mode such that the light emitted from the light source passes through the top and bottom substrates of the fluidics cartridge before reaching the image capture device.

3. The method of claim 1, wherein the capturing operation includes capturing multiple raw 2-D images, the one or more processors performing at least one of sample particle identification and sample particle tracking between the multiple raw 2-D images.

4. The method of claim 1, wherein the capturing operation includes capturing, in the raw 2-D image, a plurality of separate and distinct particle diffraction patterns corresponding to an associated plurality of particles of interest.

5. The method of claim 1, wherein the image reconstruction includes reconstructing the raw 2-D image at multiple different focalization planes in a manner that is z-plane independent, where the z-plane corresponds to an illumination direction in which the light projects from the light source.

6. The method of claim 1, further comprising sizing the image capture device to capture the raw 2-D image in a single capture event to form an image data set at a select point in time.

7. The method of claim 1, further comprising utilizing the one or more processors to automatically analyze the reconstructed image to identify the one or more particles of interest.

8. The method of claim 1, wherein the fluidics cartridge is substantially transparent to the light emitted by the light source and traveling through the cartridge retention zone.

9. The method of claim 1, wherein the fluidics cartridge comprises droplet operations electrodes arranged along at least one of the top and bottom substrates to control sample droplet manipulation when activated and deactivated.

10. The method of claim 9, wherein the light source and image capture device operate in a reflection mode with a nontransparent fluidics cartridge, wherein the nontransparent fluidics cartridge comprises a reflective layer disposed over the bottom substrate and droplet operations electrodes.

11. The method of claim 1, wherein the droplet record comprises a list of particles and their corresponding size.

12. The method of claim 1, wherein each of the one or more bins is assigned a particle size range, such that the grouping of particles into one or more bins is based on the size of the particle.

13. The method of claim 1, wherein the removing of particles from the droplet record is based on whether the particle has a size that is smaller than a predetermined lower threshold, or a size that is greater than a predetermined upper threshold.

14. The method of claim 1, wherein the analysis of the reconstructed 3-D image further comprises:
   (f) moving the sample droplet away from the cartridge illumination zone, returning the sample droplet back to the cartridge illumination zone, and repeating (a) through (e) in order to reduce overlapping particles and improve count accuracy.

15. A method for performing microfluidics imaging, comprising:
   positioning a fluidics cartridge at a cartridge illumination zone, the fluidics cartridge including top and bottom substrates separated by a droplet operations gap, the droplet operations gap configured to retain a filler fluid including at least one sample droplet containing one or more particles of interest;
   emitting light onto the cartridge illumination zone;
   capturing a raw two-dimensional (2-D) image containing a particle diffraction pattern corresponding to the one or more particles of interest utilizing an image capture device that is held in a predetermined relation relative to the light source and cartridge illumination zone; and utilizing one or more processors for analysis of reconstructed 3-D images to track cells in the sample droplet, wherein the analysis comprises:
(a) identifying, using the one or more processors, cells in a 3-D image and assigning a unique identifier to each cell;
(b) identifying, using the one or more processors, criteria of interest associated with each cell and classifying the cells based on the criteria of interest to yield cell classifications;
(c) forming, using the one or more processors, a droplet record based on the cell classifications;
(d) analyzing, using the one or more processors, the cell classifications in the droplet record and removing cells that do not satisfy the criteria of interest; and
(e) moving the sample droplet away from the cartridge illumination zone, returning the sample droplet back to the cartridge illumination zone, and repeating (a) through (d) to generate a new droplet record.

16. The method of claim 15 wherein the criteria of interest includes one of cell size, cell health, cell shape or cell transparency.

17. The method of claim 15 wherein the criteria of interest includes cell health and cells are classified as live, dead, or damaged.

18. The method of claim 15 wherein the cell classifications are based on threshold values of the criteria of interest.

19. The method of claim 15, further comprising operating the light source and image capture device operate in a reflection mode with a nontransparent fluidics cartridge that comprises a reflective layer over the bottom substrate.

20. The method of claim 15, further comprising operating the light source and image capture device in a transmission mode such that the light emitted from the light source passes through the top and bottom substrates of the fluidics cartridge before reaching the image capture device.

* * * * *

UNITED STATES PATENT AND TRADEMARK OFFICE
CERTIFICATE OF CORRECTION

PATENT NO. : 10,267,726 B2
APPLICATION NO. : 15/564416
DATED : April 23, 2019
INVENTOR(S) : Cyril Delattre et al.

Page 1 of 1

It is certified that error appears in the above-identified patent and that said Letters Patent is hereby corrected as shown below:

On the Title Page

Item [57], delete "100 jum" and insert -- 100 μm --, therefor.

Signed and Sealed this
Tenth Day of September, 2019

Andrei Iancu
*Director of the United States Patent and Trademark Office*